(12) United States Patent
Lee et al.

(10) Patent No.: US 9,528,154 B2
(45) Date of Patent: Dec. 27, 2016

(54) METHODS AND COMPOSITIONS FOR IDENTIFYING UNDIFFERENTIATED STEM CELLS AND ASSESSING CELL HEALTH

(75) Inventors: Jeannie T. Lee, Weston, MA (US); Li-Feng Zhang, Jalan Bahar (SG)

(73) Assignee: The General Hospital Corporation, Boston, MA (US)

( * ) Notice: Subject to any disclaimer, the term of this patent is extended or adjusted under 35 U.S.C. 154(b) by 1307 days.

(21) Appl. No.: 12/812,489

(22) PCT Filed: Jan. 12, 2009

(86) PCT No.: PCT/US2009/000180
§ 371 (c)(1),
(2), (4) Date: Sep. 28, 2010

(87) PCT Pub. No.: WO2009/089067
PCT Pub. Date: Jul. 16, 2009

(65) Prior Publication Data
US 2011/0008784 A1    Jan. 13, 2011

Related U.S. Application Data

(60) Provisional application No. 61/010,615, filed on Jan. 10, 2008.

(51) Int. Cl.
*C12Q 1/68* (2006.01)
*C12N 5/0735* (2010.01)

(52) U.S. Cl.
CPC ....... *C12Q 1/6881* (2013.01); *C12Q 2600/158* (2013.01)

(58) Field of Classification Search
CPC ....... C12Q 1/68; C12Q 1/6813; C12Q 1/6841; C12N 5/0606
USPC .......................................... 435/6.1, 6.11, 325
See application file for complete search history.

(56) References Cited

U.S. PATENT DOCUMENTS

2006/0286544 A1    12/2006    Mandal et al.

FOREIGN PATENT DOCUMENTS

| WO | WO 2008/112246 | * | 9/2008 |
|---|---|---|---|
| WO | WO-2008/112246 A2 | | 9/2008 |

OTHER PUBLICATIONS

Saretzki et al., (2007) Stem Cells, vol. 26(2), 455-464.*
Takahashi et al. (2006) Cell, vol. 126, 663-676.*
Avner et al., "X-chromosome inactivation: counting, choice and initiation," Nat Rev Genet. 2(1):59-67 (2001).
Boumil et al., "Forty years of decoding the silence in X-chromosome inactivation," Hum Mol Genet. 10(20):2225-32 (2001).
Dhara et al., "Gene trap as a tool for genome annotation and analysis of X chromosome inactivation in human embryonic stem cells," Nucleic Acid Res. 32(13):3995-4002 (2004).
Hall et al., "An ectopic human XIST gene can induce chromosome inactivation in postdifferentiation human HT-1080 cells," Proc Natl Acad Sci USA 99(13):8677-82 (2002).
Hoffman et al., "X-inactivation status varies in human embryonic stem cell lines," Stem Cells 23(10):1468-1478 (2005).
Kosciolek et al., "Inhibition of telomerase activity in human cancer cells by RNA interference," Mol Cancer Ther 2(3):209-216 (2003).
Pan et al., "Nanog and transcriptional networks in embryonic stem cell pluripotency," Cell Res. 17(1):42-49 (2007).
Schoeftner et al., "Developmentally regulated transcription of mammalian telomeres by DNA-dependent RNA polymerase II," Nat Cell Biol. 10(2): (9 pages) (2008).
Silva et al., "X-chromosome inactivation and epigenetic fluidity in human embryonic stem cells," Proc Natl Acad Sci USA 105(12):4820-5 (2008).
Takahashi et al., "Induction of pluripotent stem cells from mouse embryonic and adult fibroblast cultures by defined factors," Cell, 126(4):663-76 (2006).
Zhang et al., "Telomeric RNAs mark sex chromosomes in stem cells," Genetics. 182(3):685-98 (2009).
International Search Report for International Patent Application No. PCT/US2009/000180, mailed Sep. 3, 2009 (4 pages).
International Preliminary Report on Patentability for International Patent Application No. PCT/US2009/000180, issued Jul. 13, 2010 (5 pages).
Written Opinion of the International Searching Authority for International Patent Application No. PCT/US2009/000180, mailed Sep. 3, 2009 (4 pages).

* cited by examiner

*Primary Examiner* — Anne Marie S Wehbe
(74) *Attorney, Agent, or Firm* — Clark & Elbing LLP

(57) ABSTRACT

Disclosed herein are methods and compositions for the identification of teloRNA marks to assess the differentiation status of an individual stem cell or a population of stem cells, to diagnose whether and to what extent a stem cell or stem cell culture has already initiated cell differentiation, and to monitor the differentiation status of an individual stem cell or a stem cell culture during passage. The use of these methods and compositions to monitor the pluripotency and differentiation status of a stem cell or stem cell culture during differentiation enables the identification of undifferentiated and pluripotent stem cells prior to the initiation of differentiation. The methods and compositions can also be used to assess and maintain cell viability; to identify cells or a population of cells that are in a state of poor cell health; and to reduce cell growth or treat a diseased cell including, for example, pre-cancerous cells, cancerous cells, apoptotic cells, aging cells, cells undergoing stress, and otherwise diseased or dysfunctional cells.

16 Claims, 10 Drawing Sheets
(8 of 10 Drawing Sheet(s) Filed in Color)

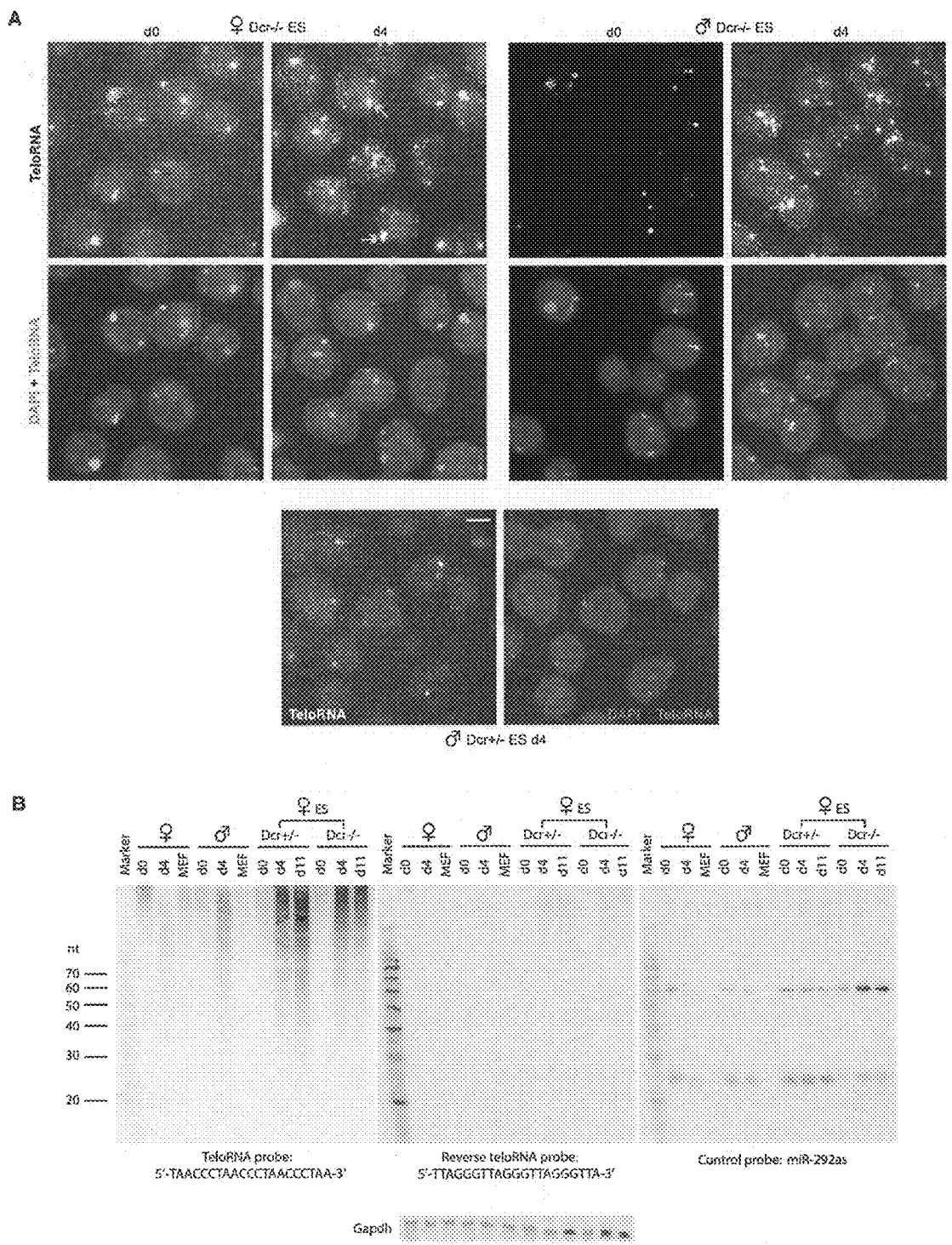
Figure 7 A-B

METHODS AND COMPOSITIONS FOR IDENTIFYING UNDIFFERENTIATED STEM CELLS AND ASSESSING CELL HEALTH

CROSS REFERENCE TO RELATED APPLICATIONS

This application is a U.S. National Stage of International Application No. PCT/US2009/000180, filed Jan. 12, 2009, which, in turn, claims the benefit of U.S. Provisional Application No. 61/010,615, filed Jan. 10, 2008, both of which are incorporated herein by reference in their entirety.

STATEMENT AS TO FEDERALLY FUNDED RESEARCH

This invention was made with Government support under Grant No.(s) GM058839 awarded by the National Institute of Health. The Government has certain rights to this invention.

BACKGROUND OF THE INVENTION

The present invention features methods for the identification and development of mammalian stem cells and their derivatives. The invention also features methods for assessing the health of mammalian cells, including both stem cells and somatic cells.

Stem cells are unique cell populations that have the ability to divide (self-renew) for indefinite periods of time, and, under the right conditions or signals, to differentiate into the many different cell types that make up an organism. Stem cells derived from the inner cell mass of the blastocyst are known as embryonic stem (ES) cells. Stem cells derived from the primordial germ cells, and which normally develop into mature gametes (eggs and sperm), are known as embryonic germ (EG) cells. Both of these types of stem cells are known as pluripotent cells because of their unique ability to differentiate into derivatives of all three embryonic germ layers (endoderm, mesoderm, and ectoderm).

The pluripotent stem cells can further specialize into another type of multipotent stem cell often derived from adult tissues. Multipotent stem cells are also able to undergo self-renewal and differentiation, but unlike embryonic stem cells, are committed to give rise to cells that have a particular function. Examples of adult stem cells include hematopoietic stem cells (HSC), which can proliferate and differentiate to produce lymphoid and myeloid cell types, bone marrow-derived stem cells (BMSC), which can differentiate into adipocytes, chondrocytes, osteocytes, hepatocytes, cardiomyocytes and neurons, and neural stem cells (NSC), which can differentiate into astrocytes, neurons, and oligodendrocytes. Multipotent stem cells have also been derived from epithelial and adipose tissues and umbilical cord blood (UCB).

A considerable amount of interest has been generated in the fields of regenerative medicine and gene therapy by recent work relating to the isolation and propagation of stem cells. The ability of stem cells to be propagated indefinitely in culture combined with their ability to generate a variety of tissue types makes the therapeutic potential from these cells almost limitless.

Although stem cells, particularly embryonic stem cells have enormous clinical potential as starting points for the generation of various replacement tissue and cells, a significant limitation to their usefulness is the requirement that the stem cells must be maintained in the undifferentiated state in cell culture. Maintaining embryonic stem cells in the undifferentiated state is very challenging, even in the hands of an experienced investigator, as a significant fraction of embryonic stem cells differentiate each time they are passaged and manipulated in culture. Furthermore, the differentiation pathway, once initiated, is irreversible. Therefore, the identification of stem cells prior to the initiation of differentiation is critical for the cells to be therapeutically useful. Current methods for testing the differentiated state of an embryonic stem cell line include the use of pluriporent stem cell markers that are unable to distinguish between undifferentiated cells and cells which have entered, at least partially, the differentiation pathway.

Improved methods are needed to assess the pluripotency of stem cells, such as embryonic stem cells, both male and female, and to identify embryonic stem cells prior to the initiation of the differentiation pathway. Such methods are needed to help realize the full therapeutic potential of these cells.

SUMMARY OF THE INVENTION

The present invention is based on the discovery of a novel cytologic mark whose expression pattern is associated with pluripotency and overall cell health. Using a Cot-1 probe or telomeric nucleic acid probe for hybridization, we have discovered that a teloRNA mark can be detected and that the teloRNA mark generally, but not necessarily, co-localizes to the sex-chromosomes in both differentiated and undifferentiated stem cells. This teloRNA mark appears to be a noncoding RNA (ncRNA) that is likely transcribed, in the outward direction, from the telomeric region of the sex chromosome. Although noncoding telomeric RNA is present on all chromosomes, the teloRNA mark generally accumulates only on the sex chromosomes of cells, specifically, the inactive X in females and the Y in males. We have previously shown that Cot-1 holes are present at the transcriptionally suppressed inactive X, and our present discoveries provide another novel relationship between Cot-1 and differentiation, namely that a region of intense Cot-1 activity (detected as a teloRNA mark) is present in proximity to the telomere, generally of the sex chromosome, and that the presence of the teloRNA mark correlates with the differentiation status of the cell.

We have discovered that expression of the number and type of teloRNA marks is tightly associated with the differentiation state of stem cells and with the overall cell health of somatic and stem cells. A cell having two teloRNA marks is undifferentiated, a cell having one teloRNA mark is differentiated, and a cell having aberrant teloRNA marks including, but not limited to, zero or greater than two marks; speckles; multiple foci; or a large cluster of speckles or multiple or no foci is a cell that is undergoing cell stress or is diseased (e.g., cancerous or pre-cancerous). Generally a cell having any deviation from the one mark (differentiated) or two marks (undifferentiated) phenotype is considered to have an aberrant teloRNA mark. In addition, we have discovered that the teloRNA mark is differentially expressed in pluripotent cells and in physiologically stressed cells. We have also discovered that dicer, an RNase III ribonuclease family member that cleaves double-stranded RNA (dsRNA) and pre-microRNA (miRNA) into short double-stranded small interfering RNA (siRNA) modulates expression of the teloRNA mark suggesting that RNAi may regulate telomeric expression.

The present invention features methods and compositions for the identification of teloRNA marks to assess the differentiation status of an individual stem cell or a population of stem cells, to diagnose whether and to what extent a stem cell or stem cell culture has already initiated cell differentiation, and to monitor the differentiation status of an individual stem cell or a stem cell culture during passage. The use of these methods and compositions to monitor the pluripotency and differentiation status of a stem cell or stem cell culture during differentiation enables the identification of undifferentiated and pluripotent stem cells prior to the initiation of differentiation. The methods and compositions can also be used to assess cell viability and to identify cells or a population of cells that are in a state of poor cell health, including, for example, pre-cancerous cells, cancerous cells, apoptotic cells, aging cells, cells undergoing stress, and otherwise diseased or dysfunctional cells. The invention also features therapeutic methods for maintaining the undifferentiated state of a cell or population of cells or maintaining the health of a cell or population of cells.

Accordingly, in a first aspect the invention features a method for determining differentiation state of a stem cell, wherein the stem cell is one of a population of stem cells. The method includes the following steps:

(a) contacting the stem cell with a Cot-1 nucleic acid probe under conditions for hybridization of the Cot-1 nucleic acid probe to a ribonucleic acid molecule in the nucleus of a stem cell; and (b) detecting the hybridization of the Cot-1 nucleic acid probe to the ribonucleic acid molecule in the stem cell, wherein the hybridization of the Cot-1 nucleic acid probe to the ribonucleic acid molecule in the stem cell is detected as a teloRNA mark. The detection can include the use of any hybridization method. RNA FISH, using high stringency hybridization on an undenatured nucleus, is one desirable method for detection of the hybridization of the Cot-1 probe to the RNA molecule in the stem cell. The presence of two teloRNA marks identifies the stem cell as a stem cell that is undifferentiated and the presence of only one teloRNA identifies the stem cell as a stem cell that is differentiated.

In one embodiment, the Cot-1 nucleic acid probe hybridizes to a telomeric repeat sequence or a subtelomeric sequence. The Cot-1 probe can include one or more, desirably three to seven, copies of the following sequence: 5' TAACCC 3' or a frameshift thereof.

In another aspect, the invention features a method for determining the differentiation state of a stem cell, wherein the stem cell is one of a population of stem cells. The method includes the following steps:

(a) contacting the stem cell with a telomeric nucleic acid probe under conditions for hybridization of the telomeric nucleic acid probe to a ribonucleic acid molecule in the nucleus of a stem cell; and (b) detecting the hybridization of the telomeric nucleic acid probe to the ribonucleic acid molecule in the stem cell, wherein the hybridization of the telomeric nucleic acid probe to the ribonucleic acid molecule in the stem cell is detected as an teloRNA mark. The detection can include the use of any hybridization method. RNA FISH, using high stringency hybridization on an undenatured nucleus, is one desirable method for detection of the hybridization of the telomeric nucleic acid probe to the RNA molecule in the stem cell. The presence of two teloRNA marks identifies the stem cell as a stem cell that is undifferentiated and the presence of only one teloRNA identifies the stem cell as a stem cell that is differentiated.

In one embodiment, the telomeric nucleic acid probe hybridizes to a telomeric repeat sequence. In another embodiment, the telomeric nucleic acid probe includes one or more, desirably three to seven, copies of the following sequence: 5' TAACCC 3' or a frameshift thereof.

In various embodiments of the above aspects, the teloRNA mark is co-localized to a sex chromosome. In another embodiment, the teloRNA mark is not co-localized to an autosomal chromosome. In embodiments where only one teloRNA is detected, the teloRNA can be co-localized to the inactive X chromosome of a female stem cell or the Y chromosome of a male stem cell. Two structures are considered co-localized if, within the resolution of light, their FISH signals show spatially overlapping or juxtaposed signals. For spatially overlapping signals, the pixels can be completely or partially superimposed on top of each other. For juxtaposed signals, the bodies occupy discrete pixel areas but the pixels are next to each other (within 1-10 pixel range).

In another aspect the invention features a method for determining the differentiation state of a stem cell culture, wherein the method includes the following steps:

(a) contacting the stem cell culture with a telomeric nucleic acid probe or a Cot-1 nucleic acid probe under conditions for hybridization of the telomeric nucleic acid probe or Cot-1 nucleic acid probe to ribonucleic acid molecules in the nuclei of stem cells in the stem cell culture; and (b) detecting the hybridization of the telomeric nucleic acid probe or Cot-1 nucleic acid probe to the ribonucleic acid molecules in the stem cells in the stem cell culture, wherein the hybridization of the telomeric nucleic acid probe or Cot-1 nucleic acid probe to the ribonucleic acid molecules in the stem cells appears as a teloRNA mark. The detection can include the use of any hybridization method. RNA FISH, using high stringency hybridization on an undenatured nucleus, is one desirable method for detection of the hybridization of the Cot-1 or telomeric nucleic acid probe to the RNA molecule in the stem cell. The presence of two teloRNA marks in a substantial portion (e.g., greater than 50%, 60%, 70%, 80%, 90% or more) of the cells in the stem cell culture identifies the stem cell culture as undifferentiated and the presence of only one teloRNA mark in a substantial portion (e.g., greater than 50%, 60%, 70%, 80%, 90% or more) of the cells in the stem cell culture identifies the stem cell culture as differentiated. A stem cell culture having a mixture of stem cells having two teloRNA marks and stem cells having only one teloRNA mark can be identified as partially differentiated.

The above aspects of the invention can also be carried out using a nucleic acid probe that hybridizes to the subtelomeric regions of the telomere.

The methods for determining the differentiation status of a stem cell or population of stem cells can be performed, once, more than once, or on multiple occasions over time. In one example, the method is used to monitor the differentiation status of the stem cell culture over time or during passage. In another embodiment, the method can be used as a preliminary screen to determine the differentiation status of a stem cell culture where, once determined, the individual stem cells can then be further assayed for the individual cell differentiation status using the methods described herein.

Optionally, any of the above methods of the invention can further include determining the presence or absence of at least one X-chromosome inactivation (XCI) marker in the stem cell. The presence of the XCI marker identifies the stem cell as a stem cell that is differentiated and the absence of the XCI marker identifies the stem cell as a cell that is undifferentiated.

The XCI marker can be any marker that is associated with XCI or the presence of an inactive X (Xi). Non-limiting examples of markers used to determine the presence or absence of XCI are described in PCT Patent Application No. PCT/US08/003,260 (Publication No. WO2008/11224) and include the Xic, Xic flanking region, Xist, Xite, Tsix, or Cot-1 and probes or primers that are substantially identical to or complementary to or can hybridize to any of these sequences, or any fragment thereof, can be used in the method to determine if the stem cell is differentiated or undifferentiated. Generally, detection of any of the presence or absence of any nucleic acids of the invention, or fragments thereof, that are associated with XCI are indicators that differentiation has been initiated in the stem cell or population of stem cells. Methods for the detection of the presence or absence of the XCI markers are described in detail in PCT Patent Application No. PCT/US08/003,260 (Publication No. WO2008/11224), which is herein incorporated by reference.

Optionally, any of the above methods of the invention can further include detecting Oct4 polypeptide expression in the stem cell or stem cell culture, wherein the presence of Oct4 expression identifies the stem cell or stem cell culture as a stem cell or stem cell culture that is undifferentiated. The above methods of the invention can also further include detecting any known polypeptide pluripotency marker, including but not limited to at least one of the following polypeptide pluripotency markers: Nanog, Rex1, alkaline phosphatase, stage specific embryonic antigen (SSEA)-1, SSEA-3, and SSEA-4, wherein the presence of a polypeptide pluripotency marker identifies the stem cell or stem cell culture as a stem cell or stem cell culture that is undifferentiated. The polypeptide pluripotency marker can be detected using any method known in the art for detection of polypeptides, such as immunological methods. In one example, the polypeptide pluripotency marker is detected using immunofluorescence which may or may not be used in combination with FISH (e.g., immunoFISH). In another embodiment of the above aspects, the method can optionally include determining the karyotype of the stem cell or stem cell culture, for example, by chromosome painting.

In another aspect the invention features a method for assessing the cell health of a cell, desirably a somatic differentiated cell, wherein the method includes the following steps:

(a) contacting the cell with a telomeric nucleic acid probe or a Cot-1 nucleic acid probe under conditions for hybridization of the telomeric nucleic acid probe or Cot-1 nucleic acid probe to ribonucleic acid molecules in the nuclei of the cell; and (b) detecting the hybridization of the telomeric nucleic acid probe or Cot-1 nucleic acid probe to a ribonucleic acid molecule in the cell, wherein the hybridization of the telomeric nucleic acid probe to a ribonucleic acid molecule in the cell appears as an teloRNA mark. The detection can include the use of any hybridization method. RNA FISH, using high stringency hybridization on an undenatured nucleus, is one desirable method for detection of the hybridization of the Cot-1 or telomeric nucleic acid probe to the RNA molecule in the stem cell. The presence of an aberrant teloRNA mark identifies the somatic differentiated cell as a cell that is under cell stress or a diseased cell. An aberrant teloRNA mark can include a teloRNA which does not appear as a single brighter than background spot after hybridization of a probe to RNA in the nucleus of a cell. An aberrant teloRNA mark can also include no foci or spots, multiple spots, freckles, speckles, or a cluster of speckles or foci. An aberrant teloRNA can also include a total number of teloRNA marks that is not the one or two marks seen in differentiated or undifferentiated cells, respectively. For example, an aberrant teloRNA can include 0, 3, 4, 5, 6, 7, 8, 9, 10 or more teloRNA marks. In one specific example, when two teloRNA marks are detected in a differentiated somatic cell, the cell is identified as a cancer stem cell. In this specific scenario, two teloRNA marks are considered aberrant teloRNA marks because two teloRNA marks would not normally be present in a differentiated somatic cell.

In various embodiments of the above aspect, the cell is mammalian (e.g., human, mouse, agricultural animal). The hybridization method can include any hybridization method and RNA FISH is one desirable method. The method can be carried out in vitro or in vivo in a subject.

In various embodiments of the above aspect, the cell stress is oxidative stress, heat shock, genotoxic stress, nutritional stress, microbial stress, or aging. The diseased cell can be a cancerous or precancerous cell, an infected cell, or an autoimmune disorder cell.

In various embodiments of any of the above aspects, the nucleic acid probe used to detect the teloRNA mark, is a Cot-1 probe, a telomeric probe, or a subtelomeric probe. The probe can be a riboprobe, a DNA probe, or an RNA probe and can be synthesized as an oligo and labeled directly. The probe can also be a double stranded plasmid, for example a T7 or Sp6 expression vector, that includes a nucleic acid sequence that is substantially identical to a Cot-1 or telomeric nucleic acid sequence, the complementary sequence, or any fragment thereof. Desirably, the probe is detectably labeled. Non-limiting examples of labels include fluorophores, enzymatic labels, and radiolabels.

For any of the aspects of the invention, the Cot-1 or telomeric nucleic acid probe can hybridize to a telomeric repeat sequence, for example, at the telomere of a sex chromosome. Although hybridization can occur at any stringency, high stringency is preferred. Desirably, the telomeric probe is a forward probe. Also desirably, the telomeric probe includes at least 1, 2, 3, 4, 5, 6, 7, 8, 9, 10, 11, 12, 13, 14, 15, 16, 17, 18, 19, 20, or more copies of the following repeat sequence: TAACCC, or any frameshift thereof. Exemplary frameshifts of the telomeric repeat sequence include AAC-CCT or ACCCTT. Desirably the probe includes three to seven copies of the repeat sequence, or a frameshift thereof.

In yet another aspect, the invention features a method of maintaining cell viability in a cell, including a somatic cell or stem cell, that is under cell stress or that is diseased, wherein the method includes contacting the cell with an siRNA molecule that hybridizes to a telomeric ncRNA in the cell, wherein the siRNA molecule includes at least one TAACCC repeat, the complementary sequence, or frameshift thereof, in an amount and for a time sufficient to decrease the levels or activity of the telomeric ncRNA in the cell.

In another aspect, the invention features a method of treating a diseased cell, wherein the method includes contacting the cell with an siRNA molecule that hybridizes to a telomeric ncRNA in the cell, wherein the siRNA molecule includes at least one TAACCC repeat, the complementary sequence, or frameshift thereof, in an amount and for a time sufficient to decrease the expression levels or activity of the telomeric ncRNA in the cell. Non-limiting examples of a diseased cell include a cancer cell and in one desired embodiment, the method results in cell death of the cell.

In another aspect, the invention features a method of reducing cell growth in a cell or population of cells, wherein the method includes contacting the cell or population of cells with an siRNA molecule that hybridizes to a telomeric ncRNA in the cell, wherein the siRNA molecule includes at least one TAACCC repeat, the complementary sequence, or frameshift thereof, in an amount and for a time sufficient to reduce the growth of the cell or population of cells. Non-limiting examples of a diseased cell include a cancer cell. In one desired embodiment the siRNA molecule is an shRNA molecule.

In another aspect, the invention features a method of maintaining the pluripotency of a stem cell. The method includes contacting the stem cell with an siRNA molecule that hybridizes to telomeric ncRNA in the cell, wherein the siRNA molecule includes at least one TAACCC repeat, the complementary sequence, or frameshift thereof, in an amount and for a time sufficient to decrease the expression levels of the telomeric ncRNA in the stem cell.

For any of the aspects of the invention, the stem cell is an embryonic stem cell, which can be male or female. Mammalian embryonic stem cells or embryonic stem cells from any agricultural animal are particularly useful in the methods of the invention. In preferred embodiments the stem cell is a human or mouse embryonic stem cell. The stem cell can be an embryonic stem cell at any stage, preferably a blastocyst stage stem cell, an embryonic germ cell, or a cloned stem cell from a somatic nuclei. The embryonic stem cells can be, for example, parthogenetic, cloned, biparentally derived, derived from a preimplantation blastomere, cloned from somatic cells, a hybrid embryonic stem-somatic cell, an artificially generated stem-like cell or an iPS cell.

In additional aspects, the invention features a kit for determining the differentiation state of a stem cell or population of stem cells or a kit for assessing the cell health of a cell or a population of cells. Each of the kits includes at least one Cot-1 or telomeric nucleic acid probe, wherein the probe hybridizes to an ncRNA molecule in the nucleus of an undenatured cell, reagents used for RNA FISH, and instructions for the use of the Cot-1 or telomeric nucleic acid probe or primer to determine the differentiation state of a stem cell or population of stem cells. Desirably, the Cot-1 or telomeric nucleic acid probe hybridizes to an RNA telomeric repeat sequence, for example, of a sex chromosome. The Cot-1 or telomeric nucleic acid probe can hybridize to an RNA telomeric repeat sequence or to any fragment thereof. Hybridization can occur at any stringency, but high stringency is preferred. In some embodiments, the kit also includes a hybridization buffer and instructions for fluorescent in situ hybridization. In one embodiment, the telomeric probe includes at least 1, 2, 3, 4, 5, 6, 7, 8, 9, 10 or more copies of the following telomere repeat sequence, TAACCC, or any frameshift thereof. Exemplary frameshifts of the telomeric repeat sequence include AACCCT or ACCCTT. In one example, the telomeric probe is labeled at either terminus by a fluorophore. One embodiment includes 3' labeling by a fluorophore such as Alexa488. Either the labeled probe or the reagents for labeling can be included in the kit.

Optionally, the kit can include at least one of the following (i) a Tsix nucleic acid probe or primer comprising a nucleic acid sequence that is substantially identical to the nucleic acid sequence of a Tsix nucleic acid molecule, the complementary sequence, or a fragment thereof, wherein the probe hybridizes to a Tsix nucleic acid molecule, (ii) an Xite nucleic acid probe or primer comprising a nucleic acid sequence that is substantially identical to the nucleic acid sequence of a Xite nucleic acid molecule, the complementary sequence, or a fragment thereof, wherein the probe hybridizes to a Xite nucleic acid molecule, and (iii) an Xist nucleic acid probe comprising a nucleic acid sequence that is substantially identical to the nucleic acid sequence of a Xist nucleic acid molecule, the complementary sequence, or a fragment thereof, wherein the probe hybridizes to a Xist nucleic acid molecule. Additionally or alternatively, the kit can also further include an antibody, or fragment thereof, that specifically binds to H3K27me3, H2A-K119ub1, Oct-4, Nanog, Rex1, SSEA-1, SSEA-3, SSEA-4, TRA-1-60, or TRA-1-81.

In another aspect, the invention features a kit for reducing the cell growth or treating a diseased cell or a population of cells, wherein the kit includes an siRNA molecule that hybridizes to a telomeric ncRNA in the cell, wherein the siRNA molecule includes at least one TAACCC repeat, the complementary sequence, or frameshift thereof, and wherein the kit further includes instructions for the use of the siRNA molecule to reduce cell growth or to treat a diseased cell or population of cells. The siRNAs are substantially identical to or complementary to any region of the telomeric ncRNA identified as teloRNA marks in the methods of the invention (e.g., multimers of the telomeric repeat TAACCC). The siRNAs includes any small RNA substantially identical to at least 15 nucleotides, preferably, 17, 18, 19, 20, 21, 22, 23, 24, 25, 26, 27, 28, 29, 30, 31, 32, 33, 34, or 35, nucleotides in length and even up to 50 or 100 nucleotides in length (inclusive of all integers in between) of any region of the telomeric ncRNA including, but not limited to, one or more telomeric repeat, desirably, three to seven telomeric repeats, or frameshifts thereof. It should be noted that, as described below, longer dsRNA fragments can be used that are processed into such small RNAs. Small RNAs can also include short hairpin RNAs (shRNAs) in which both strands of an siRNA duplex are included within a single RNA molecule.

By "stem cell" is meant any cell with the potential to self-renew and, under appropriate conditions, differentiate into a dedicated progenitor cell or a specified cell or tissue. Stem cells can be pluripotent or multipotent. Stem cells include, but are not limited to embryonic stem cells, embryonic germ cells, a cloned stem cell from a somatic nuclei, adult stem cells, and umbilical cord blood cells.

By "adult stem cell" or "somatic stem cell" is meant an undifferentiated cell found in a differentiated tissue that can renew itself and (with certain limitations) differentiate to yield all the specialized cell types of the tissue from which it originated. Adult stem cells are multipotent. Non-limiting examples of adult stem cells include hematopoietic stem cells, bone marrow-derived stem cells, and neural stem cells (NSC), as well as multipotent stem cells derived from epithelial and adipose tissues and umbilical cord blood (UCB).

By "embryonic stem cell" or "ES cell" or "ESC" is meant a cell, derived from an embryo at the blastocyst stage, or before substantial differentiation of the cell into the three germ layers, that can self-renew and that displays morphological characteristics of undifferentiated cells, distinguishing them from differentiated cells of embryonic or adult origin. Embryonic stem cells include, for example, a blastocyst stage stem cell, an embryonic germ cell, or a cloned stem cell from a somatic nuclei. Embryonic stem cells can be, for example, parthogenetic, cloned, biparentally derived, derived from a preimplantation blastomere, cloned from somatic cells, a hybrid embryonic stem-somatic cell, or an artificially generated stem-like cell including but not limited to the "iPS" cells generated by introduction of four transcription factors, Oct4, Sox2, KLF4, and cMyc. Exemplary morphological characteristics include high nuclear/cytoplasmic ratios and prominent nucleoli under a microscope. Under appropriate conditions known to the skilled artisan, embryonic stem cells can differentiate into cells or tissues that are derivatives of each of the three germ layers: endoderm, mesoderm, and ectoderm. Assays known in the art for the identification of an embryonic stem cell include the ability to form a teratoma in a suitable host or to be stained for markers of an undifferentiated cell such as Oct-4. Additional assays include those described herein.

By "cell health" is meant the viability state of a cell. Generally, a cell that is in poor cell health is one that is under cellular stress or one that is diseased. Non-limiting examples of types of cellular stress include oxidative, heat shock, genotoxic, nutritional, microbial, age-related, chemical, pharmacological, physiological, and exercise induced. Non-limiting examples of diseases include cancerous or pre-cancerous states, infection, and autoimmunity.

"Complementary sequence" refers to a sequence of bases that can form a double-stranded structure by matching base pairs. For example, the complementary sequence to 5'-C-A-T-G-3' (where each letter stands for one of the bases in DNA) is 3'-G-T-A-C-5'. A pair of complementary sequences may be RNA-RNA, RNA-DNA, DNA-RNA, or DNA-DNA.

By "compound" is meant any small molecule chemical compound, antibody, nucleic acid molecule, polypeptide, or fragments thereof.

By "Cot-1 fraction" is meant a subset of genomic DNA that contains the most highly repetitive elements in the mammalian genome (e.g., LINEs, SINEs, LTRs, ERVs, and telomeric repeat sequences). The entire Cot-1 fraction, or a subset thereof, can be labeled for use as a probe in the methods of the invention.

By "Cot-1 nucleic acid" is meant a nucleic acid molecule that is present in a Cot-1 fraction and that is substantially identical to a mammalian Cot-1 sequence, complementary sequences thereof, or any fragment thereof. Examples of mammalian Cot-1 nucleic acid sequence include the population of sequences that is the first to reanneal after denaturation as defined by reassociation kinetics.

By "Cot-1 probe," "Cot-1 nucleic acid probe," or "Cot-1 primer" is meant a nucleic acid molecule that hybridizes to at least a part of the Cot-1 fraction of nucleic acid molecules. In one embodiment, the Cot-1 probe includes a nucleic acid molecule that hybridizes to one or more telomeric repeats of the Cot-1 fraction. Hybridization can be at any stringency. High stringency hybridization is desirable.

By "differentiation" is meant the process whereby an unspecialized early embryonic cell acquires the features of a specialized cell such as a heart, liver, bone, nerve, or muscle cell. Differentiation can also refer to the restriction of the potential of a cell to self-renew and is generally associated with a change in the functional capacity of the cell. A "differentiated" cell can include a cell that is no longer pluripotent, a cell that has initiated differentiation, is in the process of differentiation, or has completed differentiation. An "undifferentiated" cell is one that is pluripotent and has not yet initiated the process of differentiation. It will be understood by the skilled artisan that colonies of undifferentiated cells can often be surrounded by neighboring cells that are differentiated; nevertheless, the undifferentiated colonies will persist when the population is cultured or passaged under appropriate conditions, and individual undifferentiated cells will constitute a substantial portion (e.g., at least 5%, 10%, 20%, 40%, 60%, 80%, 90% or more) of the cell population. Such individual undifferentiated cells identified by the methods of the invention can be isolated and cultured as an individual cell line. Differentiation of a stem cell can be further determined or confirmed by methods well known in the art and these include analysis for cell markers or morphological features associated with cells of a defined differentiated state. Examples of such markers and features include measurement of glycoprotein, alkaline phosphatase, and carcinoembryonic antigen expression, where an increase in any one of these proteins is an indicator of differentiation. Additional examples are described herein.

By "differentiation state" or "differentiation status" is meant the identification of a cell as differentiated or undifferentiated.

By "hybridize" is meant pair to form a double-stranded molecule between complementary polynucleotide sequences, or portions thereof, under various conditions of stringency. (See, e.g., Wahl et al. *Methods Enzymol.* 152: 399-407 (1987); Kimmel, *Methods Enzymol.* 152:507-511 (1987)) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, high stringency hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, high stringency hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton et al., *Science* 196:180-182 (1977); Grunstein et al., *Proc. Natl. Acad. Sci. U.S.A.* 72:3961-3965 (1975); Ausubel et al., *Current Protocols in Molecular Biology*, Wiley Interscience, New York, (2001);

Berger and Kimmel (*Guide to Molecular Cloning Techniques*, Academic Press, New York, (1987); and Sambrook et al., *Molecular Cloning: A Laboratory Manual*, Cold Spring Harbor Laboratory Press, New York.

The term "identity" is used herein to describe the relationship of the sequence of a particular nucleic acid molecule to the sequence of a reference nucleic acid molecule. For example, if a nucleic acid molecule has the same nucleotide residue at a given position, compared to a reference molecule to which it is aligned, there is said to be "identity" at that position. The level of sequence identity of a nucleic acid molecule to a reference nucleic acid molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, or other modifications.

A nucleic acid molecule is said to be "substantially identical" to a reference molecule if it exhibits, over its entire length, at least 51%, preferably at least 55%, 60%, or 65%, and most preferably 75%, 85%, 90%, 95%, 96%, 97%, 98%, 99%, or even 100% identity to the sequence of the reference molecule. For nucleic acid molecules, the length of comparison sequences is at least 6, 7, 8, 9, 10, 17, 18, 19, 20, 21, 22, 23, 24, 25, 26, 27, 28, 29, 30, 31, 32, 33, 34, 35, 40, 50, 60, 68, 70, 80, 90, 100, 200, 300, 400, 500, 600, 700, 800, 900, 1000, or more nucleotides up to 10 kB, 20 kB, 50 kB, 100 kB, or 150 kB or more nucleotides.

It should be noted that while protein-coding genes that are homologous generally share a significant level of homology (generally greater than 70%), the overall level of homology for noncoding genes, which includes the Cot-1 and telomeric regions referred to in the present invention, is generally less than 60%. For example, the same noncoding gene from different strains of mice have sequence variation on the order of one nucleotide change per 100 nucleotides. In another example, the sequence variation between strains can include basepair insertions, deletion, and single nucleotide polymorphisms.

By "isolated" is meant substantially free of other cellular material, or culture medium when produced by recombinant techniques, or substantially free of chemical precursors or other chemicals when chemically synthesized.

The term "label" or "label containing moiety" refers to a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound (e.g., chemically bound) to label-containing moieties or can be suitable to be so bound. A probe can be directly or indirectly labeled.

The term "direct label probe" or "directly labeled probe" refers to a nucleic acid probe whose label after hybrid formation with a target is detectable without further reactive processing of hybrid. The term "indirect label probe" or "indirectly labeled probe" refers to a nucleic acid probe whose label after hybrid formation with a target is further reacted in subsequent processing with one or more reagents to result in a detectable entity.

By "nucleic acid molecule" is meant any chain of nucleotides or nucleic acid mimetics. Included in this definition are natural and non-natural oligonucleotides, both modified and unmodified.

By "noncoding RNA" or "ncRNA" is meant a ribonucleic acid molecule that does not encode a protein. For example a non coding RNA can be genic, intergenic, or spliced out of a coding RNA.

By "probe" or "primer" is meant a nucleic acid molecule that hybridizes in a base-specific manner to a complementary strand of nucleic acid molecules. A probe can be single stranded at the time of hybridization to a target. By "base specific manner" is meant that the two sequences must have a degree of nucleotide complementarity sufficient for the primer or probe to hybridize. The primer or probe sequence is not required to be perfectly complementary to the sequence of the template. Non-complementary bases or modified bases can be interspersed into the primer or probe, provided that base substitutions do not inhibit hybridization. The nucleic acid template may also include "non-specific priming sequences" or "nonspecific sequences" to which the primer or probe has varying degrees of complementarity. The term "primer" as defined herein, is meant to encompass any nucleic acid that is capable of priming the synthesis of a nascent nucleic acid in a template-dependent process. Primers may be provided in double-stranded or single-stranded form, although the single-stranded form is preferred.

A probe or primer generally includes a nucleic acid sequence that hybridizes to at least about 15, for example about 20-25, and in certain embodiments about 40, 50, 75, 100, 200, 300, 400, 500, 600, 700, 800, 900, 1000, or more (up to the full length of the nucleic acid molecule) consecutive nucleotides of a nucleic acid molecule of the invention. Desirably, the probe is at least 70%, 80%, 85%, 90%, 95%, 96%, 97%, 98%, 99%, or 100% identical to the nucleic acid molecule or the complement thereof to which the probe or primer hybridizes. Optionally, the probe or primer can also include a label, including but not limited to a radioisotope, fluorescent compound, enzyme, or enzyme co-factor.

By "proliferation" is meant the expansion of a population of cells by the continuous division of single cells into two identical daughter cells.

By "purified" is meant separated from other components that naturally accompany it. Typically, a compound (e.g., nucleic acid) is substantially pure when it is at least 50%, by weight, free from proteins, antibodies, and naturally-occurring organic molecules with which it is naturally associated. Preferably, the compound is at least 75%, more preferably, at least 90%, and most preferably, at least 99%, by weight, pure. A substantially pure compound may be obtained by chemical synthesis, separation of the factor from natural sources, or production of the compound in a recombinant host cell that does not naturally produce the compound. Nucleic acid molecules may be purified by one skilled in the art using standard techniques such as those described by Ausubel et al. *Current Protocols in Molecular Biology*, John Wiley & Sons, New York, (2000). The nucleic acid molecule is preferably at least 2, 5, or 10 times as pure as the starting material, as measured using polyacrylamide gel electrophoresis, column chromatography, optical density, HPLC analysis, or western analysis.

"RNAi," also referred to in the art as "gene silencing" and/or "target silencing," refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes. The unifying features of RNA silencing phenomena are the production of small RNAs, at least 15 nt in length, preferably 15-32 nt, most preferably 17 to 26 nt in length, that act as specificity determinants for down-regulating gene expression and the requirement for one or more members of the Argonaute family of proteins (or PPD proteins, named for their characteristic PAZ and Piwi domains). Recently it has been noted that larger siRNA molecules, for example, 25 nt, 30 nt, 50 nt, or even 100 nt or more, can also be used to initiate RNAi. (See for example, Elbashir et al., *Genes & Dev.* 15:188-200 (2001), Girard et al., *Nature* 442:199-202 (2006), Aravin et al., *Nature* 442:203-207 (2006), Grivna et al., *Genes Dev.* 20:1709-1714 (2006), and Lau et al., *Science* 313:363-367 (2006)).

The term "small RNA" is used throughout the application and refers to any RNA molecule, either single-stranded or double-stranded" that is at least 15 nucleotides, preferably, 16, 17, 18, 19, 20, 21, 22, 23, 24, 25, 26, 27, 28, 29, 30, 31, 32, 33, 34, or 35, nucleotides in length and even up to 50 or 100 nucleotides in length (inclusive of all integers in between). Preferably, the small RNA is capable of mediating RNAi. As used herein the phrase "mediates RNAi" refers to (indicates) the ability to distinguish which RNAs are to be degraded by the RNAi machinery or process. Included within the term small RNA are "small interfering RNAs" and "microRNA." In general, microRNAs (miRNAs) are small (e.g., 17-26 nucleotides), single-stranded noncoding RNAs that are processed from approximately 70 nucleotide hairpin precursor RNAs by Dicer. Small interfering RNAs (siRNAs) are of a similar size and are also non-coding, however, siRNAs are processed from long dsRNAs and are usually double stranded (e.g., endogenous siRNAs). siRNAs can also include short hairpin RNAs (shRNAs) in which both strands of an siRNA duplex are included within a single RNA molecule. Small RNAs can be used to describe both types of RNA. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the small RNA or internally (at one or more nucleotides of the RNA). Nucleotides in the RNA molecules of the present invention can also comprise non-standard nucleotides, including non-naturally occurring nucleotides or deoxyribonucleotides. Small RNAs of the present invention need only be sufficiently similar to natural RNA that it has the ability to mediate RNAi.

By "reducing the growth of a cell" or "reducing cell growth" is meant a decrease (e.g., by at least 10%, 20%, 30%, 40%, 50%, 60%, 70%, 80%, 90%, 95%, 100% or more) in the rate of cell growth or cell proliferation of an individual cell or a population of cells. Cell growth can be measured using standard cell proliferation assays known in the art, non-limiting examples of which include $^3$H labeling and BrdU labeling of DNA. In one example, the proliferation rate is determined over time with a reduction being a decrease in proliferation rate of a cell or population of cells over time. In another example, the proliferation rate of a cell or population of cells is determined and compared to a reference cell or population of cells, for example, cells that are untreated or treated with a control. In one example, one cell population is treated with shRNA directed against sense RNA strands (treated) and a second control cell population is treated with shRNA directed against antisense RNA strands (control), wherein the treated cells show reduced cell growth if the growth or proliferation rate is decreased as compared to the growth or proliferation rate of the control cells.

By "telomere" is meant a section of DNA occurring at the extreme ends of each chromosome in a eukaryotic cell. Telomeres include highly repetitive sequences of nucleic acids that do not code for proteins (noncoding), but function as caps to keep chromosomes from fusing together and keep the chromosome ends from being recognized as DNA breaks. The repetitive structure of telomeres is also critical to maintain the length of the telomere, as the telomere DNA is shortened after each round of DNA replication. The telomeric DNA can be transcribed into RNA transcripts which do not code for proteins (ncRNA).

By "telomeric repeat" is meant any sequence of nucleic acids which is repeated more than one time (e.g., 2, 3, 4, 5, 6, 7, 8, 9, 10, or more) at the telomere of a chromosome. While subtelomeric sequences vary among organisms, all telomeres contain a G-rich simple repeat, with their very termini being a single-stranded 3' protrusion of the G's called the G-quartet. Generally, a telomeric repeat, once transcribed, is an ncRNA (i.e., does not code for proteins). One exemplary telomeric repeat sequence is a sequence that is complementary to a multimer of 5'-TAACCC-3', or any frameshift thereof.

By "telomeric probe" or "telomeric nucleic acid probe" is meant a nucleic acid molecule that hybridizes to at least a part of the telomere. In one embodiment, the telomeric probe hybridizes to a telomeric repeat. In one embodiment, the telomeric probe or primer includes at least 1, 2, 3, 4, 5, 6, 7, 8, 9, 10, or more, and most preferably 3 to 7 copies of the following telomeric repeat sequence: 5'-TAACCC-3', or any frameshift thereof. Optionally the telomeric repeat sequences in the probe are contiguous. Hybridization can be at any stringency. High stringency hybridization is desirable.

By "subtelomeric probe" is meant a nucleic acid molecule that hybridizes to at least a part of the subtelomeric region of a chromosome. The subtelomeric region of a chromosome lies proximal to the telomeric repeat but is not as well conserved between organisms. The subtelomeric region may also be transcribed into ncRNA.

By "teloRNA," "RNA pinpoint mark," "Cot-1 pinpoint," "Cot-1 appendage," "Cot-1 foci," or "Cot-1 structure" is meant a cytologic mark that is detected as a single brighter than background spot after hybridization of a nucleic acid probe to RNA in the nucleus of a cell. The teloRNA can be a mark, cluster, focus, domain, pinpoint, or appendage, that is generally, although not necessarily, found colocalized with an X or Y chromosome in the nucleus of a normal (e.g., differentiated or undifferentiated) cell. Desirably the nucleus is an undetanured nucleus. The colocalization of the teloRNA mark can be to the telomeric repeat region or subtelomeric region sequences of an X or Y chromosome. In female ES cells, the teloRNA is generally larger and sometimes has a more cloud like appearance. While not wishing to be limited to the particular sizes, the size of a teloRNA mark is generally 0.2-0.4 μm while the size of the teloRNA mark in female mouse ES cells is generally larger and can be as large as 0.6 to 1 μm or larger.

By "aberrant teloRNA mark" refers to a difference in the teloRNA mark, whether by characteristic or by overall number, from the teloRNA mark, as defined above. An aberrant teloRNA mark can include a teloRNA which does not appear as a single brighter than background spot after hybridization of a probe to RNA in the nucleic of a cell. An aberrant teloRNA mark can also include no foci or spots, multiple spots, freckles, speckles, or a cluster of speckles or foci. An aberrant teloRNA can also include a total number of teloRNA marks that is not the one or two marks seen in differentiated or undifferentiated cells, respectively. For example, an aberrant teloRNA can include 0, 3, 4, 5, 6, 7, 8, 9, 10 or more teloRNA marks. It should be noted that in differentiated somatic cells, two teloRNA marks is considered an aberrant teloRNA mark because a differentiated cell would normally have one teloRNA mark and the presence of two teloRNA marks is indicative that the somatic cell has initiated or completed a de-differentiation process and may be indicative of a cancer stem cell.

By "X chromosome inactivation" or "XCI" is meant the process in which one X-chromosome is shut off in the female cell (XX) to compensate for having an extra X-chromosome as compared to the male (XY) cell. The process of XCI is controlled by a master regulatory region called the X-inactivation center (Xic), which contains a number of unusual noncoding genes that work together to ensure that XCI takes place only in the XX female, only on one chromosome, and in a developmentally specific manner. At the Xic, three noncoding genes, Xist, Tsix, and Xite, are involved in this process and each makes RNA instead of protein. Xist is made only from the future inactive X and makes a 20 kb RNA that "coats" the inactive X, thereby initiating the process of gene silencing. Tsix is the antisense regulator of Xist and acts by preventing the spread of Xist RNA along the X-chromosome. Thus, Tsix designates the future active X. Xite works together with Tsix to ensure the active state of the X. Xite makes a series of intergenic RNAs and assumes special chromatin conformation. Its action enhances the expression of antisense Tsix, thereby synergizing with Tsix to designate the future active X. Together Tsix and Xite control the "choice" step, while Xist controls the "silencing" step. Tsix and Xite also regulate counting and mutually exclusive choice through X-X pairing. Thus, the control of XCI rests on the dynamic interplay between these three noncoding genes.

By "XCI marker" is meant any marker that is associated with XCI or the presence of an inactive X (Xi). Non-limiting examples of nucleic acid markers of XCI include the Xic, Xic flanking region, Xist, Xite, or Tsix. Another exemplary XCI marker is the presence of an inactive X chromsome (Xi), wherein the absence of an Xi identifies the stem cell as undifferentiated. The presence of the Xi can be detected in a number of ways. In one example, the Xi is detected using a Cot-1 probe, where the absence of Cot-1 hybridization to the X-chromosome is detected as a Cot-1 hole and where the presence of a Cot-1 hole is a positive indicator of an Xi or by the presence of Xi heterochromatin in the stem cell. The Xi can also be detected by the presence of any histone modification. In one example, the presence of Xi heterochromatin is detected by detecting the presence of H3-K27me3 hypermethylation or the presence of H2A-lysine 119 ubiquitination, for example using antibodies that specifically bind to the H3-K27me3 or H2A-lysine 119-ubiquitin, where the presence of H3-K27me3 or H2A-lysine 119 ubiquitin is a positive indicator of an Xi. Methods for detecting XCI markers and their use for determining the differentiation state of a stem cell or stem cell population are described in detail in PCT Patent Application No. PCT/US08/003,260 (Publication No. WO2008/11224), herein incorporated by reference.

Stem cell differentiation is an irreversible process and commitment to the differentiation pathway reduces or prevents the clinician's or investigator's ability to modify the stem cell in a way that is therapeutically useful. The enormous therapeutic potential of stem cells relies on the clinician's or investigator's ability to identify undifferentiated and pluripotent cells that have not yet initiated the differentiation pathway. The present invention provides novel methods for identifying stem cells prior to initiating the irreversible differentiation pathway. The present invention is based on the discovery that a teloRNA mark can be identified using a Cot-1 or telomeric nucleic acid probe, and that expression of the number and type of teloRNA marks is tightly associated with the differentiation state of stem cells and with the overall cell health of somatic and stem cells. Two teloRNA marks are detected in undifferentiated cells and generally localize or co-localize to the sex chromosomes. Once differentiation has occurred, the teloRNA marks are reduced to one mark, generally on the inactive X chromosome of the female or the Y chromosome of the male. Somatic differentiated cells are similarly marked by only one teloRNA mark whereas diseased or stressed cells, such as precancerous or cancerous cells, or cells undergoing stress, can be identified by the presence of multiple or aberrant teloRNA marks (i.e., any type of marks differing from the 1 or 2 seen in differentiated or undifferentiated cells). It should be noted that the presence of two marks in a known somatic differentiated cell is considered aberrant and may indicate that the cell initiated or completed a de-differentiation process and may be a cancer stem cell.

Based on these discoveries, the present invention features the use of a Cot-1 or telomeric nucleic acid probe to identify cells that are undifferentiated or pluripotent and can be used for therapeutic purposes, such as regenerative medicine and gene therapy. Stem cell cultures can also be screened to identify individual cells or populations of cells within the culture that are undifferentiated and these individual cells or populations of cells can be further propagated. The methods can also be used to identify cells, including stem cells or somatic cells, or a population of either type of cells) that are healthy and those that are diseased or under stress. The invention also features therapeutic methods that include the use of compounds such as siRNA to downregulate the telomeric ncRNA to maintain the pluripotency of a cell or population of cells or to restore or maintain cell health to a cell or population of cells.

Other features and advantages of the invention will be apparent from the following Detailed Description, the drawings, and the claims.

BRIEF DESCRIPTION OF THE DRAWINGS

The application file contains drawings executed in color (FIGS. 1A-1H, 2A-2C, 3A-3D, 4A-4D, 5A-5G, 6A-6E, 7A, and 9A-9B). Copies of this patent or patent application with color drawings will be provided by the Office upon request and payment of the necessary fee.

FIG. 1A is a series of photomicrographs showing sequential RNA/DNA FISH in transformed female fibroblasts. RNA FISH to detect Cot-1 pinpoints (Cy3, white arrow) and Xist RNA (FITC) was followed by slide denaturation and DNA FISH using an X-chromosome paint (FITC) to detect all Xs (yellow arrows). Scale bars 2µ. FIG. 1B is a photomicrograph showing magnification of a nucleus to demonstrate the spatial relationship between the Xi (green) and the Cot-1 pinpoint (red). FIG. 1C is a series of photomicrographs showing treatment with RNAseA prior to RNA FISH abolishes the Cot-1 pinpoint signals. FIG. 1D is a graph showing the patterns of Cot-1 pinpoint expression in transformed female fibroblasts. n=67. FIG. 1E is a graph showing the frequency with which the Cot-1 pinpoint is attached to Xi versus Xa. FIG. 1F is a series of photomicrographs showing sequential RNA/DNA FISH in primary male fibroblasts. RNA FISH to detect Cot-1 pinpoints (Cy3, red) was followed by DNA FISH using an X (FITC, green) and Y (Cy3, pseudocolored blue) paint. FIG. 1G is a photomicrograph showing magnification of a nucleus to demonstrate spatial relationship between the Cot-1 pinpoint and the Y. FIG. 1H is a graph showing the patterns of Cot-1 pinpoint expression in primary male fibroblasts. n=121.

FIG. 2A shows a summary of Cot-1 localization in fibroblast cell lines carrying Xic transgenes on an autosome ($A^{Tg}$). FIG. 2B is a series of photomicrographs showing RNA FISH of a representative nucleus (π2.5.5 clone) combining Cot-1 (Cy3, red) and Xist (FITC, green) probes. FIG. 2C is a series of photomicrographs showing RNA FISH detecting Xist (FITC) and Cot-1 RNA (Cy3), followed by slide denaturation and X-painting (FITC, grayscale shown) in an XaXi$^{\Delta Xist}$ clone.

FIG. 3A is a series of photomicrographs showing RNA FISH detecting Cot-1 RNA (Cy3, grayscale), followed by slide denaturation and DNA FISH with X (FITC) and Y (Cy3) painting probes. Representative cells from d0 male ES cells. Scale bar, 5μ. FIG. 3B is a graph showing the pattern of Cot-1 RNA expression in d0 XY ES cells. n=121. FIG. 3C is a series of photomicrographs showing RNA FISH detecting Cot-1 RNA (Cy3), followed by slide denaturation and DNA FISH with X-painting probes (FITC). Representative cells from d0 female ES cells. FIG. 3D is a graph showing the pattern of Cot-1 RNA expression in d0 XX ES cells. n=98.

FIG. 4A is a series of photomicrographs showing dual color RNA FISH on undenatured nuclei using a Cot-1 probe (Cy3) in combination with the telomeric oligo probe (TAACCC)$^7$-Alexa-488 (green). Scale bar 5μ. FIG. 4B is a photomicrograph showing RNA FISH with the reverse-strand oligo probe (GGGTTA)$^6$-Alexa-488 (green). FIG. 4C is a photomicrograph showing that the telomeric probe titrates away the Cot-1 pinpoint signal. FIG. 4D is a photomicrograph showing DNA FISH on denatured nuclei using labelled (TAACCC)$^7$ shows the distribution of all telomeres.

FIG. 5A is a series of photomicrographs showing RNA FISH detecting teloRNA (Alexa-488, shown in grayscale) followed by DNA FISH using X-(FITC) and Y-(Cy3) chromosome paints in d4 male ES cells. Arrow, teloRNA. FIG. 5B is a graph showing patterns of teloRNA expression in d4 male ES cells. FIG. 5C is a graph showing the patterns of teloRNA expression in d10 male ES cells. FIG. 5D is a series of photomicrographs showing the qualitative difference in the teloRNA foci of male versus female ES cells. Inset shows magnifications of the boxed signal. Scale bar, 1μ. FIG. 5E is a series of photomicrographs showing RNA FISH detecting teloRNA followed by DNA FISH using X-painting probes in d4 female ES cells. FIG. 5F is a graph showing the patterns of teloRNA expression in d4 female ES cells. FIG. 5G is a table showing the patterns of teloRNA expression relative to Xist expression in d10 female ES cells.

FIG. 6A is series of photomicrographs showing teloRNA FISH in d0 Tsix−/− cells. FIG. 6B is a series of photomicrogaphs showing irradiation induces telomeric RNA upregulation in MEF cells. FIG. 6C is a series of photomicrographs showing aberrrant classes of hESC exhibit abnormal telomeric RNA expression. FIG. 6D is a graph showing expression patterns of telomeric RNA in Class I, II, and III hESC lines. FIG. 6E is a series of photomicrographs showing TeloRNA FISH in the wildtype and cancer cell lines indicated. Arrows, cells with single teloRNA pinpoint. Asterisk, cells with speckling. Unmarked cells have no detectable teloRNA foci at all.

FIG. 7A is a series of photomicrographs showing RNA FISH for teloRNA (Alexa-488) in d4 Dcr−/− and control Dcr+/− ES cells. Arrows, sex-linked teloRNA. Scale bar 5μ. FIG. 7B shows northern analysis of teloRNA in d0, d4, and d11 ES cells and in MEFs (primary mouse embryonic fibroblasts). FIG. 7C shows a northern analysis using increased starting material and blots that are trimmed to eliminate the highest molecular weight RNA species in order to visualize smaller species more effectively. The two images shown are different contrasts of the same blot. Arrows, 25-nt species.

FIG. 8A shows a map of Dcr and the targeting construct (a generous gift of G. Hannon). Open boxes, DCR exons. Gray boxes, targeted RNAse III domain of Dcr. Black box, Southern probe. Black triangles, FRT sites. Open triangle, loxP sites. S, SpeI. FIG. 8B shows the results of a Southern analysis of wildtype and Dcr mutants using SpeI digestion. FIG. 8C is a graph showing quantitative realtime RT-PCR analysis of Dcr transcripts on d0, d2, d4, and d10 in wild type and representative Dcr 2 lox/− and Dcr−/− female ES clones. All values are normalized to expression of the housekeeping gene, β actin.

FIG. 9A is a series of micrographs showing expression of telomeric RNA is not visibly altered in cells carrying either sense or anti-sense shRNA vectors against telomeric RNA. FIG. 9B is a graph showing growth rates are reduced by greater than 2-fold in ES cells harboring shRNAs directed against the sense telomeric RNA. The mean growth rates and standard errors are shown. Similar results were obtained in two independent biological replicates.

DETAILED DESCRIPTION

Figure 1:
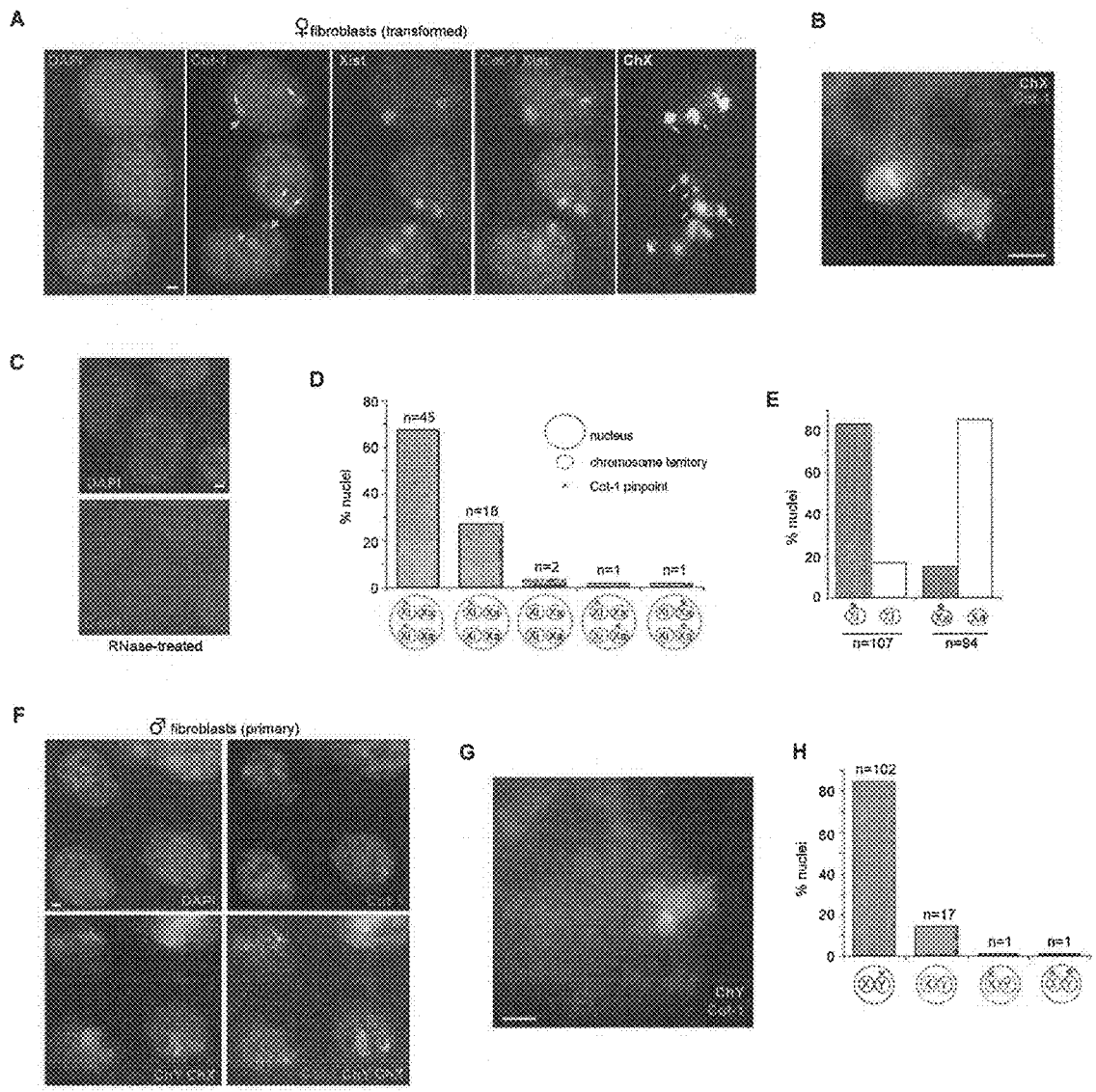
FIGS. 1A-1H show Cot-1 RNA attachment to the sex heterochromatin in the mouse.

Stem cells have enormous clinical potential because of their ability to self-renew indefinitely and to differentiate into a large number of cells and tissue types; however, their potential use in regenerative therapy and gene therapy depends on the ability of the clinician or researcher to identify those stem cells that have not differentiated or initiated the differentiation pathway. Methods for identifying undifferentiated and fully pluripotent stem cells prior to the initiation of differentiation are needed. In addition, methods for the identification of diseased or stressed cells (e.g., cancerous or precancerous), either in vitro or in vivo, are also needed. Such methods can be used, for example, as a diagnostic tool to identify cells in cell culture that are diseased or stressed, and may not be optimal for research or clinical therapeutic uses, or for in vivo identification of cells that are diseased.

In mammals, each female cell transcriptionally inactivates one of the two X chromosomes in order to balance the X-link gene dosage between male (XY) and female (XX) cells. The process of XCI is controlled by a master regulatory region called the X-inactivation center (Xic), which contains a number of noncoding genes, including three noncoding genes, Xist, Tsix, and Xite. The inactivated X chromosome (Xi) is "coated" by Xist RNA (Xi specific transcript). Xist is transcribed specifically from Xi and coats the Xi from which it is transcribed. Coating of Xist RNA recruits other silencing factors onto the chromosome and establishes chromosome-wide gene silencing. Xist RNA coating is visualized in RNA fluorescence in situ hybridization (FISH) as a bright cloud signal (see FIG. 1A). The area covered by Xist RNA is the chromosome territory of Xi, which contains no or very low levels of transcriptional activity.

General transcription level over the Xi domain can be visualized by RNA FISH on undenatured nuclei using labeled Cot-1 DNA as probe (Hall et al., *Proc. Natl. Acad. Sci. U.S.A.* 99:8677-8682 (2002), Huynh et al., *Nature* 426:857-862 (2003)). Cot-1 is the fraction of genomic DNA that reanneals first when genomic DNA is denatured into single-stranded form. The Cot-1 fraction comprises highly repetitive elements and includes repeats such as LINEs, SINEs, LTR/ERVs, and various simple repeats including telomeric repeat sequences. While subtelomeric sequences vary among organisms, all telomeres contain a G-rich simple repeat, with their very termini being a single-stranded 3' protrusion of the G's called the G-quartet. When genomic DNA is sonicated into small fragments, denatured and re-annealed, the repetitive DNA elements re-anneal much faster than single copy-genes, because repetitive elements, existing in multiple copies, are able to find their homologous partners more easily. When Cot-1 probes are used in RNA FISH on undenatured nuclei, the probes hybridize to transcribed repetitive elements, which are mainly the repetitive sequences embedded within introns and 5' or 3' UTRs of mRNA. Thus, Cot-1 probes mainly detect nascent transcripts, which contain un-spliced introns enriched for these repetitive elements. Cot-1 RNA FISH will diffusely label the mammalian nucleus and leave 'holes' in domains enriched for heterochromatin and other untranscribed sequences. Xist RNA and the Xi reside within such "Cot-1 holes" as shown in FIG. 1A.

However, while Cot-1 probes may predominantly detect unspliced intronic regions of nascent transcripts, they can also detect RNAs transcribed from intergenic repeat elements. We have discovered that, while Cot-1 probes leave a distinct hole in the Xist RNA-coated Xi, they intriguingly detect a novel structure, which we have termed the teloRNA mark, that generally co-localizes to the sex chromosomes (FIG. 1A, white arrows). (Note: cells shown are transformed tetraploid female fibroblast carrying two or more Xist clouds in each cell.) The teloRNA mark generally appears as brighter-than-background pinpoint signals. The teloRNA mark may or may not come in contact with the Xi territory but it does not reside within it.

We have discovered that in undifferentiated mouse embryonic stem cells (mESC), both X-chromosomes of the female are marked by the teloRNA marks. Both the X and the Y of the male are similarly marked. Both XX and XY undifferentiated cells are marked by two teloRNA marks. Once differentiation has occurred, the number of teloRNA marks then decreases to one. We have also discovered that this ateloRNA foci differentiation precedes Xist upregulation and XCI making it a marker of loss of pluripotency that can be detected prior to the XCI markers as described previously in PCT Patent Application No. PCT/US08/003,260 (Publication No. WO2008/11224). In somatic cells such as fibroblasts, only one of the sex chromosomes (or "the sex heterochromatin") is marked by the teloRNA mark. It is generally the inactive X (Xi) of the female and the Y of the male that is marked. The pattern of expression of the teloRNA mark is tightly associated with pluripotency and differentiation states and can be used to identify the differentiation states of mammalian cells. Without wishing to be bound by a single theory, these discoveries suggest that there is a change in telomeric RNA expression at the onset of cell differentiation. Thus, the invention provides novel methods for the identification of undifferentiated and pluripotent cells and for monitoring and maintaining the differentiation state of the cells during passage in cell culture.

We have also discovered that in diseased or stressed cells the pattern of expression of teloRNA marks is detected as an aberrant pattern. The invention also provides novel methods for assessing the overall cell health of a cell or population of cells and for maintaining cell health in a cell or population of cells.

Identification of Differentiation Status of Stem Cells

Embryonic stem cells (ESC) have enormous clinical potential because they are pluripotent cells that can, in principle, differentiate into any cell type in our body. Therefore, they are envisioned as starting points for the generation of various replacement tissue, such as cartilage, bone, muscle, neurons, pancreatic cells, and blood cells. However, in order for ESC to retain full potential to differentiate into any tissue type, they must be maintained in culture in the 'undifferentiated' state. Maintaining ESC in the undifferentiated state is very tricky, even in the hands of an experienced investigator.

We have identified methods of determining the differentiation status of stem cells that include the use of a Cot-1 or telomeric nucleic acid probe to identify teloRNA marks, which we have found to be tightly associated with the differentiation status of a stem cell. An undifferentiated and pluripotent stem cell has two teloRNA marks.

Stem cells identified as undifferentiated and pluripotent using the methods of the invention can be used as the starting point for the generation of replacement tissue or cells, such as cartilage, bone or bone cells, muscle or muscle cells, neuronal cells, pancreatic tissue or cells, liver or liver cells, fibroblasts, and hematopoetic cells. The undifferentiated stem cells can also be used for research purposes for the study of differentiation or development, and for the generation of transgenic animals useful for research purposes. The stem cells identified by the methods described herein can be used, for example, to identify signaling pathways or proteins involved in differentiation processes, which can lead to the identification of future therapeutic targets for the treatment of a variety of diseases. The undifferentiated stem cells identified by methods of the invention can also be used to study the effects of a particular gene or compound on stem cell differentiation, development, and tissue generation or regeneration.

The methods for the detection of teloRNA marks, as described herein, can be used to classify an existing or newly derived or newly obtained stem cell or embryonic stem cell or population of cells as differentiated or undifferentiated. The methods can also be used to classify a population of cells as differentiated, partially differentiated, undifferentiated, or mixed or partially differentiated. For the mixed or partially differentiated stem cell populations, the methods can be used to identify and then cull out pluripotent undifferentiated cells from those that have partially begun to differentiate. As described below, the methods of the invention can be used on ES cells of any mammalian origin including stem cells derived from preimplantation blastomeres (Chung et al., Nature 439:216-219 (2006), Klimanskaya et al., Nature 444:481-485 (2006)); stem cells cloned from somatic tissues; hybrid ES-somatic cells generated by fusion of ES cells and a somatic cell type (Cowan et al., Science 309:1369-1373 (2005)); and artificially generated ES-like cells obtained by de-differentiation of somatic cells such as described recently (Takahashi et al., Cell 126:663-776 (2006)).

This invention can be used to identify undifferentiated and pluripotent cells that are of mammalian origin, including stem cells derived by any means and in any mammalian system for research, agricultural, or clinical use. Mammalian embryonic stem cells (e.g., human or mouse) or embryonic stem cells from any agricultural animal are particularly useful in the methods of the invention.

TeloRNA Marks

As described above, we have discovered that Cot-1 or telomeric nucleic acid probes detect a novel structure, which we have termed the teloRNA mark.

We have discovered that in mouse cells, the teloRNA marks co-localized to the telomeres and can be detected by labeling of the simple telomeric repeat, $(TAACCC)^7$ (wherein the 7 indicates the number of times the sequence is repeated). This finding suggests that the teloRNA signals are RNAs preferentially transcribed from the telomeric regions of sex heterochromatin. It is worth noting that the TAACCC repeat is present on all ends of chromosomes, both autosomal and sex chromosomal in nature, yet are transcribed only from the sex chromosomes in mouse cells.

The function of the sex chromosome-associated telomeric RNAs are as yet unknown but may include maintenance of telomere integrity, which in turn maintains chromosome stability. Without the protection of the telomere, chromosome ends are recognized as DNA double-strand breaks. Consequently, chromosome loss, fusion, or translocation occurs. While not wishing to be bound by a particular theory, the fact that sex heterochromatin's telomere is specifically transcribed suggests that sex heterochomatin's telomere may need special maintenance.

All sex chromosomes show telomeric transcription in the pluripotent state but after differentiation, only the Xi of the female and the Y of the male (the sex heterochromatin) are marked by the teloRNA marks. Therefore, as described above, the expression patterns of the teloRNA marks are tightly associated with the pluripotent state.

Nucleic Acid Probes

The methods and kits of the invention include the use of a Cot-1 or telomeric (or subtelomeric) nucleic acid probe to identify teloRNA marks in a cell or population of cells.

The Cot-1 fraction contains the most highly repetitive elements in the mammalian genome (e.g., LINEs, SINEs, LTRs, and ERVs). As described above, when Cot-1 probes are used in RNA FISH on undenatured nuclei, the probes hybridize to transcribed repetitive elements, which are mainly the repetitive sequences embedded within introns and 5' or 3' UTRs of mRNA. Cot-1 RNA FISH will diffusely label the mammalian nucleus and leave 'holes' in domains enriched for heterochromatin and other untranscribed sequences.

However, while Cot-1 probes may predominantly detect unspliced intronic regions of nascent transcripts, they can also detect RNAs transcribed from intergenic repeat elements and, as described herein, detect a teloRNA mark that co-localizes to the sex chromosomes. Accordingly, the Cot-1 nucleic acid probes used in the methods of the invention can include the entire Cot-1 fraction, or any one or more of the highly repetitive elements of the Cot-1 fraction. The Cot-1 probe includes telomeric sequence and subtelomeric sequences and can be used to detect hybridization to the telomeric or subtelomeric regions of the chromosomes. A skilled artisan will be able to determine the optimal sequences to be used for the probes.

Telomeric nucleic acid probes that can hybridize to or are substantially identical to at least a part of a telomeric sequence can also be used in the methods of the invention. Desirably, the telomeric nucleic acid probes hybridize to a telomeric sequence at high stringency. In one embodiment, the telomeric nucleic acid probe includes at least 1, preferably 2, 3, 4, 5, 6, 7, 8, 9, 10, or more copies of the telomeric repeat sequence, TAACCC, or any frameshift thereof. In one example, the telomeric nucleic acid probe includes 3 to 7 copies of the telomeric repeat sequence, TAACCC, or its frameshifted derivatives including AACCCT, ACCCTA, CCCTAA, CCTAAC, or CTAACC.

Telomeric nucleic acid probes useful in the methods of the invention are strand-specific 'forward' probes. A forward probe detects the transcription of the telomeres in an outward (i.e., directed towards the ends of the telomeres) direction.

Subtelomeric probes can also be used in the methods of the invention. Subtelomeric probes hybridize to at least a part of the subtelomeric region of a chromosome which lies proximal to the telomeric repeat but is not as well conserved between organisms. The subtelomeric region may also be transcribed into ncRNA.

Any of the nucleic acid probes of the invention are designed to selectively form duplex molecules with complementary stretches of genes or RNAs or to provide primers for amplification of DNA or RNA from tissues. The nucleic acid probes, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. Therefore, nucleic acid probes of almost any length can be used, with the total length being limited by the ease of preparation and use in the intended hybridization protocol.

Generally, the probe includes a region of nucleic acid sequences that hybridizes to at least about 15, for example about 20-25, and in certain embodiments about 40, 50, 75, 100, 200, 300, 400, 500, 600, 700, 800, 900, 1000, or more consecutive nucleotides that are substantially identical to a nucleic acid molecule of the invention or the complementary sequence thereof. A probe can even contain a region of nucleic acid sequence up to the full length of the nucleic acid molecule, including any integers in between. Desirably, the probe or primer includes a contiguous stretch of nucleotides that is at least 70%, 80%, 85%, 90%, 95%, 96%, 97%, 98%, 99%, or 100% identical to a Cot-1, telomeric, or subtelomeric nucleic acid sequence or the complement thereof.

The nucleic acid probes used in the methods of the invention are prepared using methods known in the art. The skilled artisan will understand how to select, modify, label, and prepare a probe that is specific to the nucleic acid molecules of the invention. As described above, RNA based detection methods are preferred. Probes can include single-stranded RNA probes, riboprobes, double-stranded plasmid, and PCR probes. Such probes can be purchased commercially or prepared, for example, using the methods described herein. In one example, various fragments from a Cot-1 or telomeric repeat region are cloned into a T7 or SP6 expression vector and riboprobes are then synthesized using the T7 or SP6 polymerase. This method enables detection of a specific sense or antisense strand. Double-stranded plasmid or PCR probes covering the entire region can also be used when strand-specific information is not desired. Desirably, the probes will be riboprobes, or a cocktail of random fragments ranging in size from 200 to 1000 bp of sequence.

For single stranded probes, standard methods are used to generate RNA fragments from isolated DNA fragments. For example, a method developed by Green et al. (Green et al., Cell 32:681-694 (1983)), is commercially available from Promega Biotechnology (Madison, Wis.) under the tradename "Riboprobe." Other transcription kits suitable for use with the present invention are available from United States Biochemical Corporation (Cleveland, Ohio) under the tradename "Genescribe."

Methods for Detection of TeloRNA Marks

The nucleic acid probes of the invention are used to detect TeloRNA marks using any hybridization method known in the art. The results of the hybridization assay can be viewed using any microscopy technique known in the art. Because the detected pinpoint mark is RNA, and likely ncRNA, desired hybridization methods and probes will allow the detection of RNA. Exemplary assays useful for the detection of the TeloRNA marks include in situ hybridization, and fluorescent in situ hybridization (described in detail below). Preferred methods are cytologic methods which enable analysis at the single-cell level.

Three factors influence the staining sensitivity of the hybridization probes: (1) efficiency of hybridization (fraction of target DNA that can be hybridized by probe), (2) detection efficiency (i.e., the amount of visible signal that can be obtained from a given amount of hybridization probe), and (3) level of noise produced by nonspecific binding of probe or components of the detection system.

Generally in situ hybridization comprises the following major steps: (1) fixation of cells, tissue or biological structure to be examined, (2) prehybridization treatment of the biological structure to increase accessibility of target DNA, and to reduce nonspecific binding, (3) hybridization of the heterogeneous mixture of probe to the DNA in the biological structure or tissue; (4) posthybridization washes to remove probe not bound in specific hybrids, and (5) detection of the hybridized probes of the heterogeneous mixture. The reagents used in each of these steps and their conditions of use vary depending on the particular situation.

In preparation for the hybridization methods, the probe, regardless of the method of its production, may be broken into fragments of the size appropriate to obtain the best intensity and specificity of hybridization. As a general guideline concerning the size of the fragments, if the fragments are too long they are not able to penetrate into the target for binding and instead form aggregates that contribute to background noise to the hybridization; however, if the fragments are too short, the signal intensity is reduced.

In certain embodiments, it will be advantageous to include a label with the nucleic acid probe. A wide variety of appropriate nucleic acid labels are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase is used, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

While any hybridization technique can be used to detect the teloRNA marks, one preferred technique is fluorescent in situ hybridization (FISH). FISH is a cytogenetic technique which can be used to detect and localize the presence or absence of specific DNA or RNA sequences on chromosomes. FISH incorporates the use of fluorescently labeled nucleic acid probes which bind only to those parts of the chromosome with which they show a high degree of sequence similarity. Fluorescence microscopy can be used to find out where the fluorescent probe bound to the chromosome. The basic steps of FISH are outlined below and detailed protocols for RNA and DNA FISH are provided in the Examples below.

For FISH, a probe is constructed that is long enough to hybridize specifically to its target (and not to similar sequences in the genome), but not too large to impede the hybridization process. Probes are generally labeled with fluorophores, with targets for antibodies, with biotin, or any combination thereof. This can be done in various ways, for example using random priming, nick translation, and PCR using tagged nucleotides.

Generally, a sample or aliquot of a population of stem cells (stem cell culture) is used for FISH analysis. For example, in one method of preparation, cells are trypsinized to disperse into single cells, cytospun onto glass slides, and then fixed with paraformaldehyde before storing in 70% ethanol. For preparation of the chromosomes for FISH, the chromosomes are firmly attached to a substrate, usually glass. After preparation, the probe is applied to the chromosome RNA and starts to hybridize. In several wash steps all unhybridized or partially hybridized probes are washed away. If signal amplification is necessary to exceed the detection threshold of the microscope (which depends on many factors such as probe labeling efficiency, the kind of probe, and the fluorescent dye), fluorescent tagged antibodies or strepavidin are bound to the tag molecules, thus amplifying the fluorescence.

An epifluorescence microscope is used for observation of the hybridized sequences. The white light of the source lamp is filtered so that only the relevant wavelengths for excitation of the fluorescent molecules arrive onto the sample. Emission of the fluorochromes happens, in general, at larger wavelengths, which allows one to distinguish between excitation and emission light by mean of another optical filter. With a more sophisticated filter set, it is possible to distinguish between several excitation and emission bands, and thus between several fluorochromes, which allows observation of many different probes on the same strand.

Depending on the probes used, FISH can have resolution ranging from huge chromosomes or tiny (~100 kilobase) sequences. The probes can be quantified simply by counting dots or comparing color.

In some embodiments, DNA FISH is also performed (e.g., a combination of RNA and DNA FISH) to confirm the co-localization of the teloRNA mark to the sex chromosomes. Methods for DNA FISH are known in the art. It should be noted that while for RNA FISH the nuclei are undenatured, for DNA FISH the nuclei would be denatured, for example, by heating, which separates the two strands and allows access of the nucleic acid probe to the complementary region on the chromosome.

Cell Types

The methods of the invention can be used on any cell type. For determination of differentiation status, stem cells or embryonic stem cells are used. Embryonic stem cells are derived from the inner cell mass of preimplantation embryos, have been recognized as the most pluripotent stem cell population, and are therefore one of the preferred cells for the methods of the invention that include determining the differentiation status of the cell. These cells are capable of unlimited proliferation in vitro, while maintaining the capacity for differentiation into a wide variety of somatic and extra-embryonic tissues. ES cells can be male (XY) or female (XX), and both can be used in the methods of the invention.

ES cells can be directly derived from the blastocyst or any other early stage of development, or can be a "cloned" stem cell line derived from somatic nuclear transfer and other similar procedures. ES cells can include, for examples, ES cells cloned from somatic cells; hybrid ES-somatic cells generated by fusion of ES cells and a somatic cell type (Cowan et al. *Science* 309:1369-1373 (2005)); and artificially generated ES-like cells (iPS) obtained by de-differentiation of somatic cells such as described recently (Takahashi et al. *Cell* 126:663-776 (2006)). Multipotent, adult stem cells can also be used in the methods of the invention.

Preferred adult stem cells include hematopoietic stem cells (HSC), which can proliferate and differentiate throughout life to produce lymphoid and myeloid cell types; bone marrow-derived stem cells (BMSC), which can differentiate into various cell types including adipocytes, chondrocytes, osteocytes, hepatocytes, cardiomyocytes and neurons; and neural stem cells (NSC), which can differentiate into astrocytes, neurons, and oligodendrocytes. Multipotent stem cells derived from epithelial and adipose tissues and umbilical cord blood cells can also be used in the methods of the invention.

Stem cells can be derived from any mammal including, but not limited to, mouse, human, and primates. Stem cells from agricultural mammals can also be used (e.g., cow, pig, and horse), for example, from the generation of pure-bred lines and genetically engineered lines. Preferred mouse strains for stem cell preparation include 129, C57BL/6, and a hybrid strain (Brook et al., *Proc. Natl. Acad. Sci. U.S.A.* 94:5709-5712 (1997), Baharvand et al., *In Vitro Cell Dev. Biol. Anim.* 40:76-81 (2004)). Methods for preparing mouse, human, or primate stem cells are known in the art and are described, for example, in Nagy et al., *Manipulating the mouse embryo: A laboratory manual*, 3$^{rd}$ ed., Cold Spring Harbor Laboratory Press (2002); Thomson et al., *Science* 282:1145-1147 (1998), Marshall et al., *Methods Mol. Biol.* 158:11-18 (2001); Thomson et al., *Trends Biotechnol.* 18:53-57 (2000); Jones et al., *Semin. Reprod. Med.* 18:219-223 (2000); Voss et al., *Exp. Cell Res.* 230:45-49 (1997); and Odorico et al., *Stem Cells* 19:193-204 (2001).

General methods for culturing mouse, human, or primate ES cells from a blastocyst can be found in Appendix C of the NIH report on stem cells entitled *Stem Cells: Scientific Progress and Future Research Directions* (this report can be found online at the NIH Stem Cell Information website, http://stemcells.nih.gov/info/scireport). For example, in the first step, the inner cell mass of a preimplantation blastocyst is removed from the trophectoderm that surrounds it. (For cultures of human ES cells, blastocysts are generated by in vitro fertilization and donated for research.) The small plastic culture dishes used to grow the cells contain growth medium supplemented with fetal calf serum, and are sometimes coated with a "feeder" layer of nondividing cells. The feeder cells are often mouse embryonic fibroblast (MEF) cells that have been chemically inactivated so they will not divide. Additional reagents, such as the cytokine leukemia inhibitory factor (LIF), can also be added to the culture medium for mouse ES cells. Second, after several days to a week, proliferating colonies of cells are removed and dispersed into new culture dishes, each of which may or may not contain an MEF feeder layer. If the cells are to be used for human therapeutic purposes, it is preferable that the MEF feeder layer is not included. Under these in vitro conditions, the ES cells aggregate to form colonies. In the third major step required to generate ES cell lines, the individual, nondifferentiating colonies are dissociated and replated into new dishes, a step called passage. This replating process establishes a "line" of ES cells. The line of cells is termed "clonal" if a single ES cell generates it. Limiting dilution methods can be used to generate a clonal ES cell line. Reagents needed for the culture of stem cells are commercially available, for example, from Invitrogen, Stem Cell Technologies, R&D Systems, and Sigma Aldrich, and are described, for example, in U.S. Patent Application Publication Numbers 20040235159 and 20050037492 and Appendix C of the NIH report, *Stem Cells: Scientific Progress and Future Research Directions*, supra.

The methods of the invention can also be used to assess the cell health of any type of cell including stem cells, embryonic stem cells, and any somatic cell. Somatic cells include any cell that is not a germline cell (e.g., sperm, ova, gametocytes, and stem cells). Examples of somatic cells include, but are not limited to, endothelial cells, epithelial cells, fibroblast cells, keratinocytes, lymphocytes, muscle cells (e.g., myocytes), nerve cells (e.g., neurons), bone cells, brain cells (e.g., glial cells), blood cells, lymph cells (e.g., lymphocytes), connective tissue cells, and somatic cell hybrids. Cells can be primary cells, undifferentiated, transformed cells, hyperplastic cells, differentiated, precancerous cells, cancerous cells, or otherwise.

Identification of the Differentiation State of Human Cells

In one embodiment, the invention features the use of Cot-1 or telomeric nucleic acid probes to determine the differentiation status of human stem cells.

We have previously shown that, despite the fact that hESC express appropriate pluripotency markers (e.g., OCT4, SSEA3/4, and Alkaline Phosphatase), these lines are not epigenetically equivalent and vary tremendously in their differentiation status. (See U.S. Provisional Patent Application No. 60/906,626.) Based on staining for various XCI markers, we identified three classes of human embryonic stem cell (hESC) lines: (I) those that are pluripotent and can undergo XCI as they differentiate (similar to mESC), (II) those that have already undergone XCI and may therefore no longer be pluripotent, and (III) those that have undergone XCI but subsequently lost XIST expression and may be undergoing X-reactivation. Class I may be the only class suitable for human stem cell therapy and is therefore the class of hESC lines that is desirable for commercial and clinical use. Class II lines are no longer pluripotent (may not be able to make all desirable cell types), and Class III may be dangerous for human therapy, as the two Xa state may be a predisposition towards cancer. Because the vast majority of hESC lines are of the Class II and III types, a diagnostic cytological mark to identify pluripotent Class I hESC lines is needed.

We have discovered that Class I lines show two teloRNA marks while Class II lines exhibit one (consistent with its partially or fully differentiated state). Class III lines show a high proportion of lines with aberrant teloRNA marks which can include multiple foci or speckles.

The teloRNA marks described herein and the methods of detecting the teloRNA marks using a Cot-1 or telomeric probe in human embryonic stem cells, human primary cells, human somatic cells, and human cancer cells can be used to determine the differentiation state of hESC and to identify human cells that are suitable for clinical or therapeutic use (e.g., cells having two teloRNA marks). The detection of aberrant teloRNA marks, as described below, can be used to identify Class III cells or cells that are not appropriate for clinical or therapeutic use.

Methods of Assessing Cell Health

The methods of the invention can also be used to assess the cell health of a cell or a population of cells. Based on our studies of the presence (and phenotypic appearance) of teloRNA marks in various cell lines, we have discovered that the pattern of teloRNA mark expression differs significantly between normal and diseased or stressed cells. An aberrant pattern of teloRNA mark expression can be used to identify diseased cells, such as cancer cells and pre-cancerous cells, or cells undergoing cell stress.

As described in detail in the Examples below, in primary mammalian cell lines, a single teloRNA mark is detected. The intensity of the teloRNA marks is weaker in human cells than those seen in the mouse and is more easily detected with telomeric oligo probe than with human Cot-1 probe, presumably because human telomeres are considerably shorter than mouse telomeres. It is known that human telomeric length ranges from 10-20 kb, while mouse telomeric length can span 20-150 kb.

As described below, the pattern of teloRNA mark expression differs significantly between normal and cancer cells. Cancer or pre-cancerous somatic cells may 'revert' to a more pluripotent state by acquiring the double pinpoint, sex-chromosome-associated signals seen normally only in undifferentiated embryonic stem cells, i.e, cancer stem cells may acquire this property seen only in normal embryonic stem cells. Alternatively, they may develop additional teloRNA pinpoint signals due to aberrant activation of autosomal telomeres.

Figure 6:
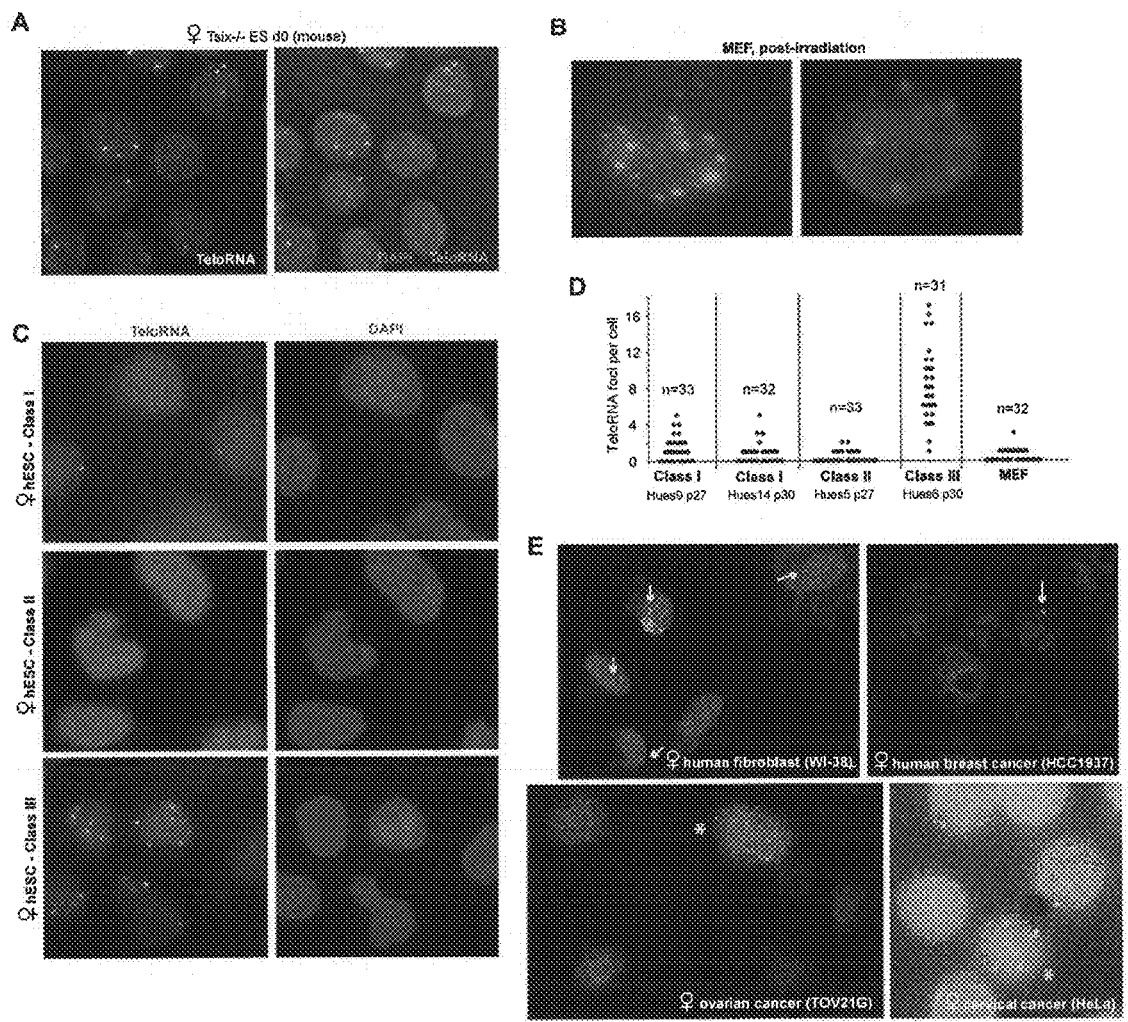
FIGS. 6A-6E show the altered teloRNA patterns in physiologically aberrant states.

Aberrant patterns of teloRNA mark expression can include any pattern of expression that is not a single discrete focus with a size comparable to the size of a single discrete focus seen in a mouse embryonic stem cell after RNA FISH using a Cot-1 probe or a telomeric probe. An aberrant pattern of expression can include, but is not limited to, multiple foci, speckles, a large cluster of signals, or zero or more than two teloRNA signals. In addition, an aberrant pattern of expression can include detection of the teloRNA at chromosomes other than the sex chromosomes. The aberrant pattern of teloRNA expression can be measured as an absolute difference (e.g., the presence of speckles or multiple foci) or a relative difference where the size and/or intensity of the signal of the teloRNA mark is compared to an teloRNA mark from a reference cell (e.g., a known healthy cell or primary cell) that is preferably, but not necessarily, from the same species. FIG. 6B provides an example of an aberrant teloRNA mark in an ovarian cancer cell line and a breast cancer cell line using a Cot-1 probe.

In the methods of the invention, the presence of aberrant teloRNA marks and the size and quantity of the teloRNA mark are used as an indicator of the overall health of the cell or cell line.

In one example, the methods of the invention can be used to diagnose malignant and pre-cancerous states and also potentially identify the de-differentiated cancer stem cells. The methods described herein would allow a clinician to detect a cancer cell or population of cells at an early stage and enable diagnosis and treatment of the cancer at an early stage, possibly before full-blown malignancy. In addition, the ability of the methods to detect the cell health and disease status of a single cell would allow for the identification of a single cancer cell and possibly a cancer stem cell and allow for monitoring or treatment of a subject having the cancer cell prior to development of the tumor or tumor metastases. The methods can also be used to assess cells that remain during or after definitive surgery to remove the tumor to determine if a cancer stem cells or cancer cells remain after the surgery. Such cytological methods can be used to identify and desirably increase the disease free margins remaining after surgical removal of a tumor and thereby help to improve the prognosis of the subject.

The methods of the invention can also be used to assess the general health of any cell culture, including an ES culture. We have previously discovered that many existing hESC lines cannot undergo XCI at all after some time in culture. Due to the association of 2 active X chromosomes with cancer states, these lines are potentially very dangerous and may not be suitable to put into patients for stem cell therapy. Because the Cot-1 and telomeric probes of the invention 'diagnose' the expression state of the X-chromosome, we can use this tool to determine whether a hESC line belongs to this class (Class III, described above) of potentially dangerous hESC.

The methods of the invention can also be used to assess other disease states or to identify cells that are undergoing cell stress. In addition to cancer or pre-cancerous states, additional disease states that can be identified by the methods of the invention include auto-immune diseases, chronic inflammatory diseases, and infectious processes. Types of cell stress that can be identified by the methods of the invention include, but are not limited to, pharmacological, physiological, chemical oxidative, heat shock, genotoxic, nutritional, microbial, exercise-induced, and age related. For example, if a cell is suspected of undergoing cell stress, the methods of the invention can be carried out and, if an aberrant pattern of expression of teloRNA marks is detected, that cell is then identified as a cell undergoing cell stress.

Combination Methods

There are several established polypeptide pluripotency markers and these markers can be used in combination with one or more of the above methods to determine the differentiation state of a cell.

For example, any of the above methods to determine the differentiation status of a cell can be carried out in combination with a method for the detection of an XCI marker, wherein the presence of the XCI marker identifies the stem cell as a stem cell that is differentiated and the absence of the XCI marker identifies the stem cell as a cell that is undifferentiated.

The XCI marker can be any marker that is associated with XCI or the presence of an inactive X (Xi). Non-limiting examples of markers used to determine the presence or absence of XCI are described in PCT Patent Application No. PCT/US08/003,260 (Publication No. WO2008/11224) and include the Xic, Xic flanking region, Xist, Xite, or Tsix and probes or primers that are substantially identical to or complementary to or can hybridize to any of these sequences, or any fragment thereof, can be used in the method to determine if the stem cell is differentiated or undifferentiated. Generally, detection of the presence or absence of any nucleic acids that are associated with XCI are indicators that differentiation has been initiated in the stem cell or population of stem cells. Methods for the detection of the presence or absence of the XCI markers are described in detail in PCT Patent Application No. PCT/US08/003,260 (Publication No. WO2008/11224), which is herein incorporated by reference.

Optionally, any of the above methods for determining the differentiation status of a cell or population of cells can further include detecting Oct4 polypeptide expression in the stem cell or stem cell culture, wherein the presence of Oct4 expression identifies the stem cell or stem cell culture as a stem cell or stem cell culture that is undifferentiated. The above methods of the invention can also further include detecting any known polypeptide pluripotency marker, including but not limited to at least one of the following polypeptide pluripotency markers: Nanog, Rex1, alkaline phosphatase, surface antigens TRA-1-60 and TRA-1-81, stage specific embryonic antigen (SSEA)-1, SSEA-3, and SSEA-4, wherein the presence of a polypeptide pluripotency marker identifies the stem cell or stem cell culture as a stem cell or stem cell culture that is undifferentiated. The polypeptide pluripotency marker can be detected using any method known in the art for detection of polypeptides, such as immunological methods. In one example, the polypeptide pluripotency marker is detected using immunofluorescence which may or may not be used in combination with FISH (e.g., immunoFISH). In another embodiment, the method can optionally include determining the karyotype of the stem cell or stem cell culture, for example, by chromosome painting. A molecular profile of additional genes and proteins expressed by undifferentiated ES cells that can be used to monitor ES cell differentiation are described by Brandenberger et al., (Brandenberger et al., *BMC Dev. Bio.* 4:10 (2004)).

In addition, undifferentiated cells can be identified by the absence of markers of differentiation. Exemplary markers of differentiation include any protein or mRNA that is characteristic of a particular differentiated cell and will be known to the skilled artisan. For example, cells that have differentiated into neurons will express tyrosine hydroxylase, cells that have differentiated into oligodendrocytes will express NG2 proteoglycan, A2B5, and PDGFR-α, and will be negative for NeuN, cells that have differentiated into T lymphocytes will express CD4 and CD8, and cells that have differentiated into a mature granulocyte will express Mac-1.

Additional examples of markers of differentiated and undifferentiated cell types can be found at the in Appendix E of the NIH report stem cells entitled *Stem Cells: Scientific Progress and Future Research Directions*, (this report can be found online at the NIH Stem Cell Information website, http://stemcells.nih.gov/info/scireport). Methods for detecting the expression of protein markers, transcription factors, or surface antigens or the mRNA or genes encoding these (e.g., the Pou5f1 gene that encodes the Oct-3/Oct-4 transcription factor) are known in the art and include, for example, immunostaining, immunoblotting, immunohistochemistry, PCR, southern blotting, northern blotting, RNase protection assays, and in situ hybridization.

The undifferentiated stem cell can also be identified by its morphology. The morphology of the undifferentiated stem cell is distinct from that of the differentiated stem cell and morphological characteristics can be used in combination with the XCI markers to determine the differentiation status of the cell. Generally, ES cells are immortalized and have a rounded morphology, a high radiance level, and very little cellular outgrowth on gelatinized plates. Methods for detecting morphology of the stem cells are also known in the art.

The methods of the invention that include the detection of the teloRNA mark can be used alone or in combination with the detection of one or more of the markers of differentiation described herein or known in the art including markers of XCI or any of the protein markers of pluripotency to determine the differentiation status of a cell or cell culture. For example, in one method of the invention, detection of the teloRNA marks and detection of Tsix expression, and Xist expression are used in combination to determine the differentiation state of a stem cell. In another example, Oct4 expression is also detected. Non-limiting examples of the combined methods using XCI markers and their outcomes are provided in PCT Patent Application No. PCT/US08/003, 260 (Publication No. WO2008/11224).

The combinations described herein are provided only to illustrate the possible combinations and are not intended to limit the invention to such combinations.

Individual Cells Versus Cell Culture

The methods of the invention can be used to detect the differentiation status or overall cell health of a single cell or a population of cells. Desirably, the methods are used to detect the differentiation state of a single cell or a single cell within a culture of cells, which can then be expanded and cultured for clinical or research purposes. Techniques such as RNA FISH and immunofluorescence enable the expression of various genes and overall epigenetic states to be examined on a single-cell basis. For each of the methods, individual colonies of a stem cell line are picked and expanded as a clonal population and each one is labeled as a subline of the original colony. An aliquot of each subline is then tested by any of the methods of the invention while the remainder of the subline is either kept in culture or frozen or both. An aliquot of the subline that is designated as undifferentiated and pluripotent using the methods of the invention can then be matched back to the frozen aliquot or aliquot of cells of that subline that are kept in culture. For such techniques, the aliquot of a cell culture is analyzed by FISH or immunoFISH and then individual cells within that culture can be identified as undifferentiated and further expanded or cultured. The advantage of such techniques is that, for partially differentiated cells, they enable the determination of what fraction of the population has differentiated and what fraction remains undifferentiated and presumably still pluripotent and to identify the clonal population from which the undifferentiated cells were derived.

The methods of the invention can be used, for example, as an initial check of a cell line to determine the differentiation state or cell health (e.g., stem cell, cancer cell or stressed cell) or to monitor a presumably undifferentiated or healthy cell culture during passage (e.g., once per passage, once every other passage, once every third passage, once every two days, once every four days, or once every week as needed). If differences within the cell culture are detected over time spent in culture, individual cells can be further tested using the cytologic methods of the invention. If desired, after an initial determination of the status of the cell culture, individual cells within the culture can then be tested using the cytologic methods of the invention. In addition, an aliquot of a culture can be induced to differentiate and monitored using the cytologic methods of the invention to verify that it still follows the one teloRNA mark equals differentiated versus two teloRNA marks equals undifferentiated pattern.

For example, if, using the methods described herein, a significant fraction of the cells are still undifferentiated, the culture might be salvaged by 'culling' out colonies of cells that still maintain pristine characteristics. The 'culling' can be achieved in two ways. The first is similar to that used to 'pick' embryonic stem cells, where a 200 μl pipet tip is used to first cut a perimeter around the desired clonal clusters of embryonic stem cells (colony) and then the pipet is used to pick up the colony of interest and place it into a new culture dish. This strategy is used when the culture is dominated by already differentiated cells. The second technique is the reciprocal strategy in which the differentiated cells are removed by the pipet. This strategy is used when the colony is largely undifferentiated and only a few clusters of differentiated colonies need to be removed.

The methods of the invention can also be used on a stem cell culture to determine whether a test compound affects the differentiation state of the cells. For example, a cell culture can be assayed for teloRNA marks prior to the addition of a compound and then assayed again after the addition of the test compound. Changes in the expression of teloRNA marks in the culture would indicate that the cell culture as a whole is showing signs of undergoing differentiation.

Kits

The present invention features kits for the determination of the differentiation status of a cell or population of cells. The kits can include any of the nucleic acid probes described herein (e.g., Cot-1, subtelomeric, or telomeric probes) which can be used for the detection of teloRNA marks in a cell or population of cells. The kit can further include components useful for the detection of XCI markers or pluripotency markers. The kit can further include instructions for the use of the kit to detect the differentiation status of a cell or population of cells.

The present invention also features kits for the determination of the cell health of a cell or a cell culture. The kits can include any of the nucleic acid probes described herein which can be used for the detection of teloRNA marks in a cell or population of cells. The kit can further include instructions for the use of the kit to assess the health of a cell or population of cells.

In one example, the kit includes one or more nucleic acid molecules that are substantially identical to a Cot-1 or a telomeric nucleic acid molecule or the complementary sequence thereto and that hybridizes to a Cot-1 region or telomeric region of a chromosome, preferably a sex chromosome. Desirably, the telomeric probe includes at least 1, 2, 3, 4, 5, 6, 7, 8, 9, 10 or more copies of the 5'-TAACCC-3' repeat, or frameshifts thereof. In one example, the telomeric probe includes three to seven copies of the 5'-TAACCC-3' repeat.

In another example, the kit further includes one or more nucleic acid probes that are substantially identical to an Xic, Xic flanking region, Xist, Xite, or Tsix or the complementary sequence thereto and that hybridizes to an Xic, Xic flanking region, Xist, or Tsix nucleic acid molecule.

In one embodiment, the probe is a telomeric nucleic acid probe that includes at least one copy, desirably three to seven copies, of the nucleic acid sequence TAACCC or a frameshift thereof. In additional embodiments the probe is provided as detectably labeled or the components for labeling the probe for use in RNA FISH are provided. In one example, the probe is labeled at either terminus by a fluorophore, for example, Alexa 488.

The probes present in the kit can be a single-stranded RNA probe, a riboprobe cocktail, a PCR probe, a double-stranded plasmid, or any other type of probe that can be used to detect the expression of an TeloRNA mark and/or one or more of the Xic, Xic flanking region, Xist, or Tsix nucleic acid molecules in a cell or cells. Alternatively or additionally, the kit can include the reagents necessary to prepare the probe (e.g., a double-stranded plasmid and the relevant polymerase for transcription of the probe). The probe can be labeled for detection or the kit can include the components necessary for labeling the probe for detection. Non-limiting examples of fluorescent labels for the probes include FITC, Cy3, and Cy5.

The kits can also include hybridization buffers, wash solutions, reagents for fixing the nucleic of a cell, mounting media (with or without anti-fade and DAPI), or components useful for checking the karyotype of the cell (e.g., chromosome painting reagents to detect if there are 2 Xs in the cell and to check if the cell is diploid).

Kits of the invention can further include reagents for detecting the formation of the Xi either alone or in combination with the reagents for detecting XCI nucleic acid molecules described above. Such reagents include antibodies that specifically bind marks of Xi formation (e.g., H3K27me3 or H2A-K119ub1), antibody incubation buffers, secondary antibodies, wash solutions and/or mounting media.

Any of the kits described above can further include reagents for the detection of pluripotency markers in the cell. Such reagents include antibodies that specifically bind protein pluripotency markers (e.g., Oct4, Nanog, Rex1, SSEA-1, -3, -4), reagents for the detection of alkaline phosphatase, such as an antibody to alkaline phosphatase and reagents for detection (e.g., Chemicon Catalog No. SCR004 or the StemTag Alkaline Phosphatase Activity Assay kit from Cell Biolabs), antibody incubation buffers, secondary antibodies, wash solutions and/or mounting media.

Therapeutic Uses

We have localized the teloRNA marks to the telomeric regions of the sex chromosomes and identified them as telomeric ncRNA. Although there are various sequences present at the telomeric regions of the sex chromosomes, the data described in the Examples below suggest that the teloRNA marks are ncRNA and are likely transcribed from the telomeric repeats of the sex chromosomes. Although the function of the ncRNA is not yet known, one possibility is the maintenance of chromosomes in pluripotent cells. Our data suggest a link to cell proliferation, as knocking down teloRNA with shRNA retards cell growth by more than 2-fold. Therefore, RNAi strategies against teloRNA may be used to control aberrant proliferation in diseased cells. The present invention includes the use of small molecule compounds as therapeutics (e.g., chemical or biological compounds, or siRNAs) to downregulate the telomeric ncRNA of a sex chromosome identified as teloRNA marks. Such small molecule therapeutics can be used to treat a cancerous or pre-cancerous cell or cells or to kill the cells or to prevent them from progressing into a frank tumor or a metastases. The small molecule therapeutics can also be used to reduce cell growth or to treat other disease states which can be identified using the teloRNA detection methods described herein.

One method for downregulating the ncRNA, for example, to prevent a stem cell from differentiating in culture or to treat cancer or other disease states identified, for example, using the methods of the invention involves the use of small RNA molecules, such as siRNA, directed to the telomeric or Cot-1 sequences or flanking regions that are introduced into stem cells and prevent the stem cells from undergoing X chromosome inactivation and from differentiating in culture. Our discovery that teloRNA may be processed to 25-nt siRNA and that dicer, an RNase III ribonuclease family member that cleaves double-stranded RNA (dsRNA) and pre-microRNA (miRNA) into short double-stranded small interfering RNA (siRNA), modulates expression of the teloRNA mark suggests that RNAi may regulate telomeric expression and that siRNA molecules can be used to down-regulate the telomeric ncRNA of a sex chromosome identified as teloRNA marks. The use of such small RNA molecules circumvents the need for removal of the transgene because the small RNA molecules have a limited half-life and will naturally degrade. Exemplary methods for RNA interference (RNAi) using siRNAs are described below.

RNA Interference (RNAi)

RNAi is a form of post-transcriptional gene silencing initiated by the introduction of double-stranded RNA (dsRNA). Short 15 to 32 nucleotide double-stranded RNAs, known generally as "siRNAs," "small RNAs," or "microRNAs" are effective at down-regulating gene expression in nematodes (Zamore et al., Cell 101: 25-33 (2000)) and in mammalian tissue culture cell lines (Elbashir et al., Nature 411:494-498 (2001), hereby incorporated by reference). The further therapeutic effectiveness of this approach in mammals was demonstrated in vivo by McCaffrey et al. (McCaffrey et al., Nature 418:38-39 (2002)).

siRNAs that are substantially identical to or complementary to any region of the telomeric ncRNA identified as TeloRNA marks in the methods of the invention (e.g., multimers of the telomeric repeat TAACCC) are included as therapeutic compounds of the invention. Kits that include such siRNAs are also contemplated by the present invention. The use of such siRNAs may function to maintain chromosomes in pluripotent cells or to protect cells from becoming diseased or stressed.

The invention includes any small RNA substantially identical to at least 15 nucleotides, preferably, 17, 18, 19, 20, 21, 22, 23, 24, 25, 26, 27, 28, 29, 30, 31, 32, 33, 34, or 35, nucleotides in length and even up to 50 or 100 nucleotides in length (inclusive of all integers in between) of any region of the telomeric ncRNA including, but not limited to, one or more telomeric repeat, desirably, three to seven telomeric repeats, or frameshifts thereof. It should be noted that, as described below, longer dsRNA fragments can be used that are processed into such small RNAs. Small RNAs can also include short hairpin RNAs in which both strands of an siRNA duplex are included within a single RNA molecule.

The specific requirements and modifications of small RNA are known in the art and are described, for example, in PCT Publication No. WO01/75164, and U.S. Application Publication Numbers 20060134787, 20050153918, 20050058982, 20050037988, and 20040203145, the relevant portions of which are herein incorporated by reference. In particular embodiments, siRNAs can be synthesized or generated by processing longer double-stranded RNAs, for example, in the presence of the enzyme dicer under conditions in which the dsRNA is processed to RNA molecules of about 17 to about 26 nucleotides. siRNAs can also be generated by expression of the corresponding DNA fragment (e.g., a hairpin DNA construct). Generally, the siRNA has a characteristic 2- to 3-nucleotide 3' overhanging ends, preferably these are (2'-deoxy) thymidine or uracil. The siRNAs typically comprise a 3' hydroxyl group. In some embodiments, single stranded siRNAs or blunt ended dsRNA are used. In order to further enhance the stability of the RNA, the 3' overhangs are stabilized against degradation. In one embodiment, the RNA is stabilized by including purine nucleotides, such as adenosine or guanosine. Alternatively, substitution of pyrimidine nucleotides by modified analogs e.g. substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

siRNA molecules can be obtained through a variety of protocols including chemical synthesis or recombinant production using a Drosophila in vitro system. They can be commercially obtained from companies such as Dharmacon Research Inc. or Xeragon Inc., or they can be synthesized using commercially available kits such as the Silencer™ siRNA Construction Kit from Ambion (catalog number 1620) or HiScribe™ RNAi Transcription Kit from New England BioLabs (catalog number E2000S).

Alternatively siRNA can be prepared using standard procedures for in vitro transcription of RNA and dsRNA annealing procedures such as those described in Elbashir et al., Genes & Dev. 15:188-200 (2001); Girard et al., Nature 442:199-202 (2006); Aravin et al., Nature 442:203-207 (2006); Grivna et al., Genes Dev. 20:1709-1714 (2006); and Lau et al., Science 313:363-367 (2006). siRNAs are also obtained by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g. size exclusion chromatography), glycerol gradient centrifugation, and affinity purification with antibody can be used to isolate the small RNAs.

siRNAs specific to Cot-1 or telomeric nucleic acids can also be obtained from natural sources. Such small RNAs can be purified as described above and used in the methods of the invention.

Short hairpin RNAs (shRNAs), as described in Yu et al., Proc. Natl. Acad. Sci U.S.A. 99:6047-6052 (2002); or Paddison et al., Genes & Dev 16:948-958 (2002), incorporated herein by reference, can also be used in the methods of the invention. shRNAs are designed such that both the sense and antisense strands are included within a single RNA molecule and connected by a loop of nucleotides (3 or more). shRNAs can be synthesized and purified using standard in vitro T7 transcription synthesis as described above and in Yu et al. (supra). shRNAs can also be subcloned into an expression vector that has the mouse U6 promoter sequences which can then be transfected into cells and used for in vivo expression of the shRNA.

A variety of methods are available for transfection, or introduction, of dsRNA into mammalian cells. For example, there are several commercially available transfection reagents useful for lipid-based transfection of siRNAs including but not limited to: TransIT-TKO™ (Mirus, Cat. # MIR 2150), Transmessenger™ (Qiagen, Cat. #301525), Oligofectamine™ and Lipofectamine™ (Invitrogen, Cat. # MIR 12252-011 and Cat. #13778-075), siPORT™ (Ambion, Cat. #1631), DharmaFECT™ (Fisher Scientific, Cat. # T-2001-01). Agents are also commercially available for electroporation-based methods for transfection of siRNA, such as siPORTer™ (Ambion Inc. Cat. #1629). Microinjection techniques can also be used. The small RNA can also be transcribed from an expression construct introduced into the cells, where the expression construct includes a coding sequence for transcribing the small RNA operably linked to one or more transcriptional regulatory sequences. Where desired, plasmids, vectors, or viral vectors can also be used for the delivery of dsRNA or siRNA and such vectors are known in the art. Protocols for each transfection reagent are available from the manufacturer. Additional methods are known in the art and are described, for example in U.S. Patent Application Publication No. 20060058255.

The concentration of dsRNA used for each target and each cell line varies and can be determined by the skilled artisan. If desired, cells can be transfected multiple times, using multiple small RNAs to optimize the gene-silencing effect.

EXAMPLES

The following examples are provided for the purposes of illustrating the invention, and should not be construed as limiting.

Example 1

Telomeric Pinpoint RNAs Mark the Sex Chromosomes of Stem Cells and Somatic Cells Examples of epigenomic regulation by macroRNAs exist across all of biology. In fission yeast and plants, centric heterochromatin depends on co-transcriptional recruitment of the RNAi and silencing machineries by expressed ncRNA within retrotransposons. In the fruitfly, dosage compensation of the X-chromosome requires the action of roX1 and roX2, two macroRNAs associated with the MSL complex that directs hypertranscription of the male X-chromosome. In mammals, macroRNA function is exemplified by Xist (Borsani et al., *Nature* 351:325 (1991); Brockdorff et al., *Nature* 351:329 (1991); Brown et al., *Nature* 349:38 (1991)) and its antisense partner, Tsix (Lee and Lu, *Cell* 99:47-57 (1999))—two genes that control the initiation of 'X-chromosome inactivation' (XCI). XCI is induced by Xist RNA, a 17-kb ncRNA that accumulates in cis and recruits silencing factors to the X destined to be inactivated (Clemson et al., *J. Cell Biol.* 132:259-275 (1996); Penny et al., *Nature* 379:131-137 (1996); Wutz et al., *Nat Genet* 30:167-174 (2002)). Tsix opposes Xist through co-transcriptional recruitment of repressive chromatin to Xist (Navarro et al., *Genes Dev* 19:1474-1484 (2005); Sado et al., *Dev Cell* 9:159-165 (2005); Sun et al., *Mol Cell* 21:617-628 (2006)). These examples possibly provide only a glimpse of the full range of macroRNA capabilities used by complex genomes.

Below we describe the identification of another sex-linked macroRNA. Unlike Xist and Tsix, this RNA associates with both X and Y. Rather than enveloping the sex chromosome, the RNA appears as an appendage. The RNA also has a predilection for the heterochromatic sex chromosome in differentiated cells. Taking advantage of its various manifestations during cell differentiation, we provide evidence that the RNA can be used as a distinct tag or marker for pluripotent stem cells and aberrant cells.
Results
A New Sex Chromosome Appendage Transcriptional activity within a subnuclear region can be assessed by RNA fluorescence in situ hybridization (FISH) using Cot-1 sequences to probe undenatured nuclei (Hall et al., *Proc Natl Acad Sci USA* 99:8677-8682 (2002); Huynh and Lee, *Nature* 426:857 (2003)). 'Cot-1' refers to the DNA fraction that reanneals first after genomic DNA is denatured. Because the Cot-1 fraction is enriched for repetitive elements that are often present in the introns of newly synthesized mRNA (pre-splicing), Cot-1 probes broadly identify subnuclear regions enriched for nascent transcripts and domains with ongoing transcription.

We noted that, while the inactive X (Xi) generally excluded Cot-1 hybridization, the Xi in mouse fibroblasts showed frequent association with an intense Cot-1 body (FIG. 1A). The Cot-1 bodies were smaller than the Xist RNA clouds and appeared as a pinpoint attachment to the Xi rather than being a part of the Xi territory (FIG. 1B). RNAseA treatment abolished the signals, indicating that the Cot-1 structure is comprised of RNA (FIG. 1C). The Cot-1 bodies could be seen in virtually all cells, with 83% (n=135) attached specifically to Xi (FIG. 1D). In female cells, 82% of all Xi had one (very occasionally two) Cot-1 appendages (FIG. 1E). When the Cot-1 pinpoint was not attached to Xi, it contacted the active X (Xa) (17%, FIG. 1E). This relationship was observed in both transformed (shown) and primary female fibroblasts. Thus, while the Xi generally lacks Cot-1 expression due to a dearth of nascent transcription, a structure of intense Cot-1 activity lies immediately adjacent to the Xi.

The Xi association initially led us to suspect a connection to XCI. To our surprise, however, male fibroblasts also expressed Cot-1 pinpoints (FIG. 1F). The Cot-1 structures were attached to the Y in 83% of nuclei (FIGS. 1G,H). Conversely, 85% (n=121) of all Ys displayed a Cot-1 appendage, with the Cot-1 RNA residing at the edge of the sex chromosome territory rather than within it (FIG. 1G). Exactly one pinpoint per Y was observed in males, whereas two pinpoints were very occasionally found next to the Xi in females. Thus, the Cot-1 body is neither specific to females nor to the X.
Relationship to XCI The association with the two heterochromatic sex chromosomes (Xi and Y) is curious. To determine if there is a connection to XCI, we asked whether the Cot-1 appendage occurred in XCI-mutant cell lines. We first tested three independent male fibroblast lines carrying Xist sequences on an autosomal transgene. Previous analysis showed that Xist RNA induces ectopic silencing of the host autosome in all three cell lines (Lee et al., *Proc Natl Acad Sci USA* 96:3836-3841 (1999)). Here, however, we saw no Cot-1 attachments to any transgenic autosome (FIGS. 2A,B). We next examined female fibroblast clones in which Xist has been conditionally deleted from the Xi [XaXi$^{\Delta\Delta Xist}$ (Zhang et al., *Cell* 129:693-706 (2007)]. Previous analysis showed that the Xist deletion resulted in loss of Xi heterochromatin and partial reactivation of the Xi. Despite those changes, however, the XaXi$^{\Delta\Delta Xist}$ chromosome retained an association with the Cot-1 pinpoint at a similar frequency (FIG. 2C; Xi distinguished from Xa by its associated Cot-1 hole). Combined, these results showed that Xist expression has no immediate effect on the Cot-1 structure and argued against a direct relationship to XCI.

We then examined mouse embryonic stem (ES) cells. Female ES cells carry two Xa and are uncommitted to XCI but can recapitulate XCI upon cell differentiation ex vivo. Intriguingly, undifferentiated XX and XY ES cells displayed not one but two Cot-1 structures. XY cells showed predominantly two Cot-1 pinpoints per nucleus, one attached to the X and the other to the Y (FIGS. 3A,B). XX cells showed two subpopulations, with ~50% of nuclei exhibiting two pinpoints per nucleus and ~45% exhibiting only one (FIGS. 3C,D). In both female subpopulations, the Cot-1 structures were nearly always attached to Xa. Thus, although Xist expression does not directly impact the Cot-1 structure, the structure does bear direct relationship to the sex chromosomes in multiple cell types.
A Telomeric Origin To identify the origin of the expressed sequence, we first asked whether the Cot-1 pinpoints co-localized with Tsix RNA and might therefore originate from the X-inactivation center. Two-color RNA FISH revealed that Tsix signals are close to but not coincident with the Cot-1 pinpoints. Because LINEs, SINEs, and centromeric repeats are major components of the Cot-1 fraction, we next tested individual elements of each repeat class but found none that co-localized with the Cot-1 foci.

Figure 4:
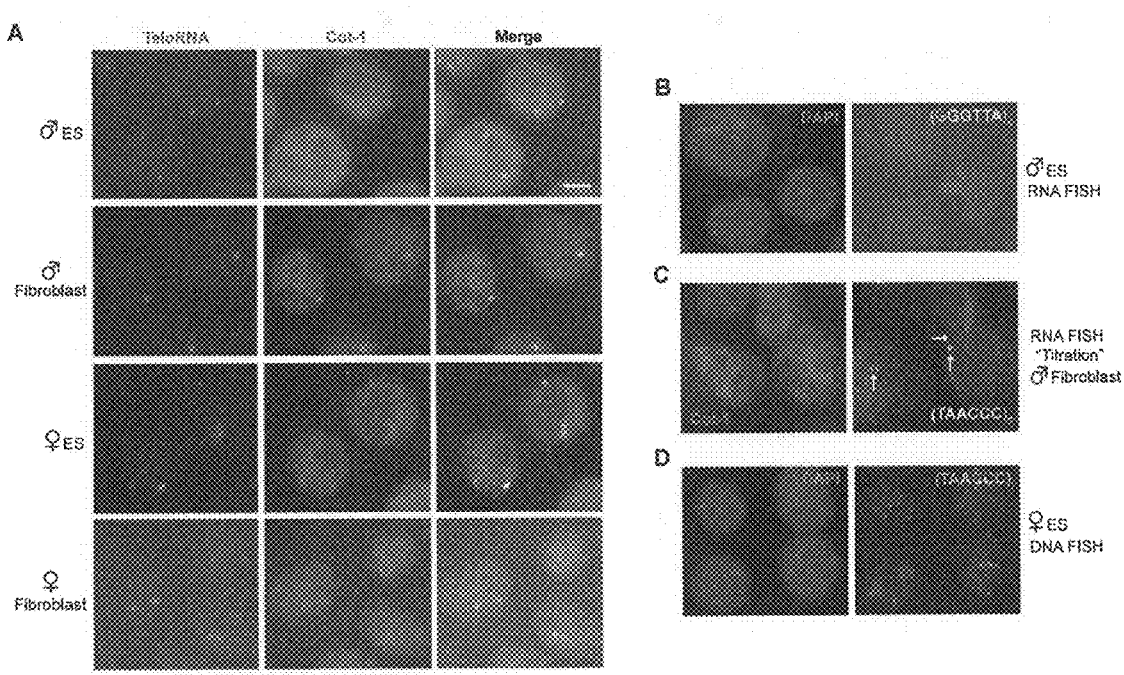
FIGS. 4A-4D show the Cot-1 RNA pinpoint mark is of telomeric origin.

The Cot-1 fraction is also known to contain telomeric repeats. While subtelomeric sequences vary among organisms, all telomeres contain a G-rich simple repeat and a single-stranded 3' protrusion of G's called the G-quartet (McEachern et al., *Annu Rev Genet* 34:331-358 (2000); de Lange, *Nat Rev Mol Cell Biol* 5:323-329 (2004)). Interestingly, using a complementary $(TAACCC)^7$ probe, we observed pinpoint RNA FISH signals that co-localized perfectly with the Cot-1 foci in all cell types (FIG. 4A). While the heterogeneous Cot-1 probe diffusely stained the nucleus in addition to the X and Y appendages, the telomeric probe gave highly specific pinpoint signals with little to no staining of other regions. The reverse probe, $(GGGTTA)^6$, gave no signal in any cell type (FIG. 4B) (Note: the G-rich probe is a 6mer, because higher oligomers were troublesome to synthesize; for the C-rich probe, 21 nt were sufficient to detect the pinpoint signals). Significantly, mixing the $(TAACCC)^7$ probe at high concentration (12.5 ng/ml or 10 pmol/µl) outcompeted the heterogeneous Cot-1 probe (20 ng/µl) and specifically abolished the Cot-1 pinpoints without affecting the staining of other nuclear regions (FIG. 4C). Thus, the Cot-1 fraction responsible for the sex-linked pinpoints is specifically the telomeric repeat. We note that the telomerase RNA primer cannot be the source because only 8 nucleotides of this 1.5 kb RNA are homologous to our probe—not enough to hybridize under our stringent conditions. We henceforth refer to the telomeric RNA as 'teloRNA'.

Figure 3:
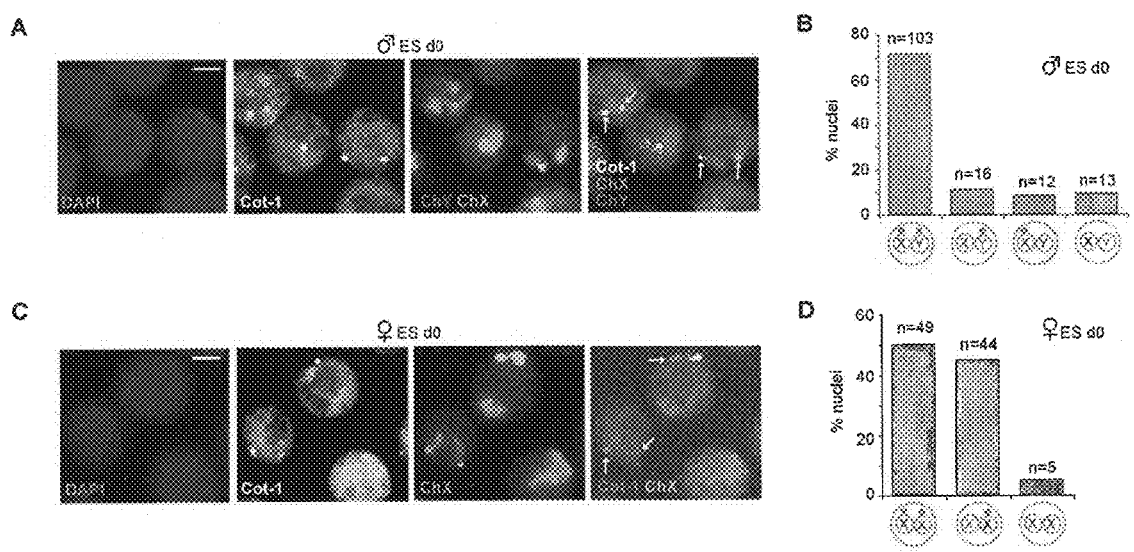
FIGS. 3A-3D shows two Cot-1 marks in undifferentiated ES cells.

These data indicate that the telomeres of at least one or two chromosomes are transcribed in the mouse and transcription occurs unidirectionally in the outward orientation. Transcription along telomeres had been reported previously in birds and trypanosomes (Rudenko and Van der Ploeg, *Embo J* 8:2633-2638 (1989)). During preparation of this manuscript, telomeric transcription was also reported in mammals ('TERRA') (Azzalin et al., Science 318:798-801 (2007); Schoeftner and Blasco, *Nat. Cell Biol.* electronic publication ahead of print (2008)). Based on our data, telomeric transcription could in principle occur generally among many or all chromosomes, as was reported concurrently (Azzalin et al., Science 318:798-801 (2007); Schoeftner and Blasco, *Nat. Cell Biol.* electronic publication ahead of print (2008)), or be restricted to the X and Y, as suggested by our staining patterns in the mouse (FIGS. 1,3). To investigate, we denatured cells and performed DNA FISH using the $(TAACCC)^7$ probe to identify all telomeres in the nucleus. A multifocal staining pattern (FIG. 4D) implied that teloRNAs do not accumulate on all telomeres but originate only from one or two chromosomes. Unlike the findings of Schoeftner et al., we conclude that the teloRNAs associate specifically with the sex chromosomes in mouse cells.

Transitional States During Cell Differentiation

Figure 5:
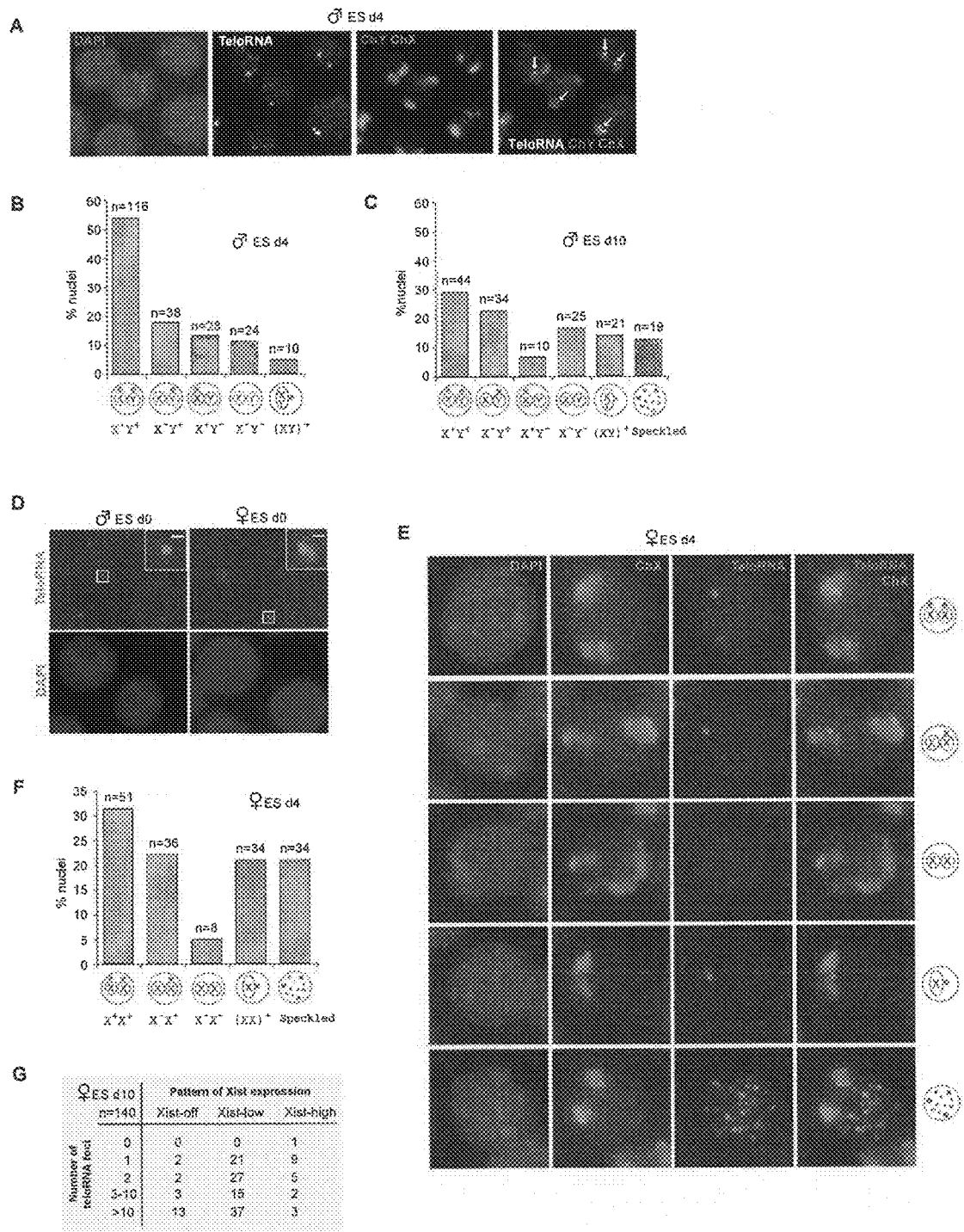
FIGS. 5A-5G show the transitional states of the TeloRNA marks in differentiating ES cells.

The differences in the number of teloRNA foci suggested that teloRNA expression is highly regulated. Indeed, analysis in the ES culture system revealed dynamic changes during differentiation. While >70% of undifferentiated male cells (day 0 [d0]) displayed two teloRNA foci (FIG. 3), cell differentiation (d4, d10) led to a progressive decrease in the percentage of nuclei with two foci $(X^+Y^+)$ and an increase in the percentage with one (FIG. 5A-5C). The single pinpoint was almost always attached to the X $(X^+Y^-)$ or the Y $(X^-Y^+)$. On d4, other patterns included those with no foci $(X^-Y^-)$ and those with a single pinpoint 'shared' between closely paired X and Y $(XY)^+$ (FIG. 5B). This may be due to the fact that the ES cells are not differentiating synchronously. By d10, the cumulative number of nuclei with a single pinpoint $[X^-Y^+, X^+Y^-, (XY)^+]$ exceeded those with two $(X^+Y^+)$ and the $X^-Y^+$ pattern becoming the predominant type. At this timepoint, an unusual pattern of multifocal, speckled staining became visible in ~12% of cells (see below). Given that >80% of XY cells showed the $X^-Y^+$ pattern in the fully differentiated cells (FIGS. 1A-1H), we believe that the patterns seen on d4 and d10 represent 'transitional states', that the $X^+Y^+$ pattern identifies the original undifferentiated state, and that the $X^-Y^+$ pattern signifies the mature differentiated state.

The teloRNA in XX ES cells also showed dynamic differentiation patterns. In general, the teloRNA foci of XX cells could be distinguished from those of XY cells by their consistently larger size (FIG. 5D). The XY foci tend to be punctate, while the XX foci bore significant resemblance to Xist RNA clouds (albeit not as large). Differentiation of XX cells also led to a progressive decrease in the percentage of nuclei with two foci $(X^+X^+)$ and the appearance of transitional patterns (FIG. 5E-5G). Whereas ~50% of d0 female cells showed the $X^+X^+$ pattern (FIGS. 3C,D), only 32% of d4 cells remained $X^+X^+$. At the same time, there was a relative increase in the total number of nuclei with a single RNA focus $[X^+X^-, (XX)^+]$. On d4, there was also the appearance of speckling, a pattern not observed in male cells until d10. Approximately 22% of nuclei showed 'paired' Xs with 'shared' telomeric RNA between them (FIGS. 5E-5F). This was potentially interesting, in light of recent reports of homologous X-chromosome pairing during cell differentiation just prior to or coincident with Xist upregulation (Xu et al., *Science* 311:1149-1152 (2006); Bacher et al., *Nat Cell Biol* 8:293-299 (2006)). The data in sum showed that female differentiation is also marked by transitional states, with the $X^+X^+$ pattern most likely representing the truly undifferentiated state and the $X^+X^-$ or $X^-X^+$ pattern representing the mature differentiated state. The fact that only 50% of d0 XX cells actually show the $X^+X^+$ pattern may reflect the tendency for XX ES cells to differentiate spontaneously.

Although mutational analysis did not reveal a direct relationship to Xist (FIGS. 2A-2C), the differentiation analysis suggested that XCI and changes to teloRNA expression occur contemporaneously (FIGS. 5A-5G). To test the relationship further, we performed Xist RNA FISH in combination with teloRNA FISH on d10 female cells. Previous work showed that Xist has three expression states (Sun, et al., *Mol Cell* 21:617-628 (2006); Panning et al., *Cell* 90:907-916 (1997); Sheardown et al., *Cell* 91:99-107 (1997)): "Low" in pre-XCI undifferentiated ES cells, where Xist transcription is poised for full activation; "high" in post-XCI differentiated female cells where Xist is fully transactivated; and "off" on the Xa of differentiated male and female cells. Among Xist$^{high}$ cells, we found that a single teloRNA focus was the most frequent pattern (FIG. 5G). The Xist$^{high}$ fraction represents cells that have undergone differentiation and XCI successfully. The occurrence of a single teloRNA focus is therefore consistent with the pattern observed in fully differentiated fibroblasts (FIGS. 1A-1H). Among Xist$^{low}$ cells (presumably still undifferentiated), one- and two-pinpoint patterns were very common, consistent with undifferentiated XX cells displaying one or two pinpoints preferentially (FIGS. 3A-3D).

Taken together, these results demonstrated that differentiation in both XX and XY cells leads to dynamic changes in teloRNA expression, with the overall effect of reducing two RNA foci in undifferentiated cells to a single RNA focus in mature differentiated cells.

Altered TeloRNA Expression in Abnormal Cells

For d10 female cells, the most common pattern among the Xist$^{low}$ subpopulation was not the two-foci pattern but the speckled pattern (52%, n=100). The speckled pattern was even more common in Xist$^{off}$ cells (80%, n=20). The Xist$^{off}$ and Xist$^{low}$ subpopulations are presumably those in which dosage compensation failed or was significantly delayed. Among d10 male cells, speckling was not common at all. These results suggested that teloRNA speckling may be a sign of stress caused, in this case, by genotoxicity associated with unrealized dosage compensation.

To determine if altered teloRNA expression could signify aberrant cell physiology, we first examined a Tsix−/− cell line (Lee, Science 309:768-771 (2005)). In this female mutant, deletion of the macroRNA gene abolishes homologous X-chromosome pairing and counting/choice, leading to an abnormal XCI profile which includes mixtures of cells with 0 Xi, 1 Xi, or 2 Xi. Growth of Tsix−/− cells results in high rate of cell death in culture (Lee), Science 309:768-771 (2005)) and in mice (Lee, Nature Genet. 32:195-200 (2002)). Here, we found that its growth in culture is marked by frequent speckling (FIG. 6A), as 64% of nuclei show multifocal staining (n=84). Thus, the Tsix mutant provides further evidence of a link between genotoxicity and altered teloRNA expression. Gamma irradiation also resulted in telomeric RNA upregulation in all MEF cells of the culture (FIG. 6B). Thus, widely different stimuli such as Dcr deficiency, radiation, and aberrant chromosome counting and inactivation are linked to changes in telomeric RNA expression in mice.

We next tested human cells. Like mouse ES cells, human embryonic stem cells (hESC) are uncommitted to XCI in the undifferentiated state but can inactivate one X during cell differentiation (Dhara and Benvenisty, 2004; Hall et al., 2008; Shen et al., 2008; Silva et al., 2008). However, recent work shows that many hESC are epigenetically abnormal with respect to XCI and can be grouped into three classes on the basis of XCI patterns (Adewumi and al., 2007; Enver et al., 2005; Hall et al., 2008; Hoffman et al., 2005; Shen et al., 2008; Silva et al., 2008). Here, we found that Class I female cells, which undergo XCI properly, exhibited either one or two telomeric RNA foci (FIGS. 6C-6D), consistent with those observed in mouse ES cells. Human telomeric RNA signals, however, are much smaller and less intense than the mouse signals, perhaps correlating with shorter human telomere lengths (Harley et al., 1990; Kipling and Cooke, 1990). Class II cells—which have already undergone XCI (Xist$^+$) and are epigenetically aberrant—generally displayed none with a small subset displaying one. At least one Class III line (HUES6)—which have presumably lost Xist expression following premature XCI and are epigenetically most abnormal—showed multifocal staining reminiscent of that seen in Tsix−/−, irradiated, and Dcr−/− cells. These data showed that aberrant dosage compensation in hESC is also associated with altered telomeric RNA expression.

In primary human female fibroblasts (WI-38), telomeric RNA expression was similar to that observed in mouse fibroblasts, with only one detectable telomeric RNA focus per nucleus (FIG. 6E). Among cancer cells of various origins, telomeric RNA patterns were distinctly different from those seen in normal cells. A majority of cells of a breast cancer line (HCC1937), an ovarian cancer line (TOV21G), and a cervical cancer line (HeLa) showed no detectable telomeric RNA foci at all, consistent with the general shortening of telomeres in cancer cells (Feldser and Greider, Cancer Cell 11:461-469 (2007); Blackburn et al., Nat Med 12:1133-1138 (2006)). In all cancer lines examined, some degree of speckling could be observed in a small subset of cells. In HCC1937, a minority of cells showed a single large focus—much brighter and larger than was seen in control WI-38 cells.

Thus, in general, telomeric RNA foci are smaller in human cells than in mouse cells, possibly reflecting shorter telomeric lengths in humans. Although telomeric foci are relatively small in humans, the pattern of expression in healthy cells clearly differs from that in stressed or diseased cells. We emphasize the fact that changes to telomeric expression in stress and disease can involve either increases or decreases in RNA foci number and size.

Effects of a Dicer Deficiency on TeloRNA

The increase in telomeric RNA foci number seen above implied that the telomere can, under some conditions, be transcribed from autosomes as well as the X and Y. This observation raised the fascinating question of how the RNA is regulated. The telomeric repeats may normally only be transcribed from sex chromosomes (transcriptional regulation); alternatively, they may be universally transcribed but accumulate only on the sex chromosomes (post-transcriptional regulation). Chromatin structure at the telomere is reminiscent of pericentric heterochromatin (Volpe et al., Science 297:1833-1837. (2002); Grewal and Elgin, Nature 447:399-406 (2007)) in that genes inserted within or near both structures are subject to long-range silencing (Tham and Zakian, Oncogene 21:512-521 (2002); Vega et al., Nat Rev Mol Cell Biol 4:948-959 (2003); Gottschling et al., Cell 63:751-762 (1990)). Given that gene regulation in the pericentric region is known to involve Dicer (Dcr) (Bernstein et al., Nature 409:363-366 (2001)) and the RNAi pathway (Volpe, et al., Science 297:1833-1837. (2002); Grewal and Elgin, Nature 447:399-406 (2007)), we asked whether teloRNA is also impacted by Dcr function.

Figure 7:
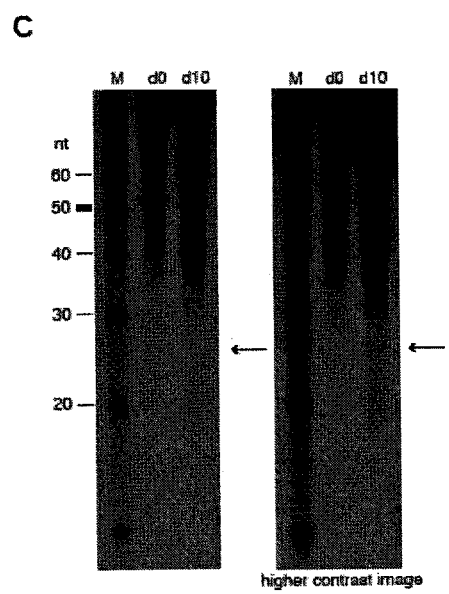
FIGS. 7A-7C show the effects of Dcr deficiency on teloRNA expression.

Using Dcr-deficient male and female ES model (FIGS. 8A-8C), we observed a modest increase in both number and size of teloRNA foci in d0 Dcr−/− cells as compared to wildtype cells (compare FIG. 7A to FIG. 3). Cell differentiation resulted in further amplification in number and intensity of teloRNA foci in Dcr−/− cells relative to Dcr+/− and Dcr+/+ cells of both sexes (d4, FIG. 7A). While there was teloRNA upregulation from many if not all chromosomes, the sex-linked teloRNA foci were particularly robust (arrows, FIG. 7A)—with the X-linked teloRNA especially so. Thus, Dcr activity indeed affects teloRNA expression and that autosomal teloRNA can accumulate when Dcr-dependent RNA processing is down-regulated.

The action of Dcr is often associated with processing to small RNAs (Grewal and Elgin, Nature 447:399-406 (2007); Zamore and Haley, Science 309:1519-1524 (2005); Bei et al., Cell 130:756 (2007)). To determine whether small RNAs are associated with telomeres, we performed Northern analysis on wildtype ES cell and fibroblasts and looked for RNAs in the 20 to 70 nt size range. While the control miR-292 RNA could be detected using the same blot, no discrete small RNA bands could be observed using the 'forward' telomeric probe (FIG. 7B). However, the telomeric probe consistently detected an RNA smear ranging in size down to 30 or 40 nt to more than 1.0 kb in all samples. By contrast, hybridization using the 'reverse' probe yielded no signals, consistent with the RNA being transcribed unidirectionally and outwardly (FIGS. 4A,B).

Because the considerably greater quantities of longer telomeric RNAs could potentially squelch probe hybridization to smaller RNAs, we repeated the Northern analysis, this time using small RNA fractions from d0 and d10 female ES cells rather than total RNA, began with greater starting material, and increased the probe length to improve small RNA detection. Intriguingly, such analysis revealed a band at ~25 nt and possibly additional bands around 20 nt (FIG. 7C). These small bands were specific to differentiated cells (d10) and not present in the d0 population. Thus, these results gave the impression that a fraction of telomeric RNAs may be processed to small RNAs in a developmentally specific manner and present the possibility that RNA turnover is regulated by the RNAi pathway in a Dcr-dependent fashion. This is consistent with the observation that Dcr-deficient cells exhibited greater telomeric RNA accumulation not only at the sex chromosomes but generally throughout the genome, as demonstrated by both RNA FISH (FIG. 7A-7B).

The smearing of signals observed using the forward probe likely results from heterogeneity in teloRNA size, which in turn may reflect unequal telomeric repeat lengths across the culture or usage of multiple transcription initiation sites within the repeat block. Consistent with the RNA FISH data, the Northern analysis showed that ES cell differentiation caused an increase in teloRNA expression and expression was most dramatically elevated in Dcr−/− cells. These data argued that, although not obviously processed to siRNAs, teloRNAs are regulated at some level by RNA processing via Dcr.

Telomeric Expression in Normal Cell Growth and Disease

Figure 9:
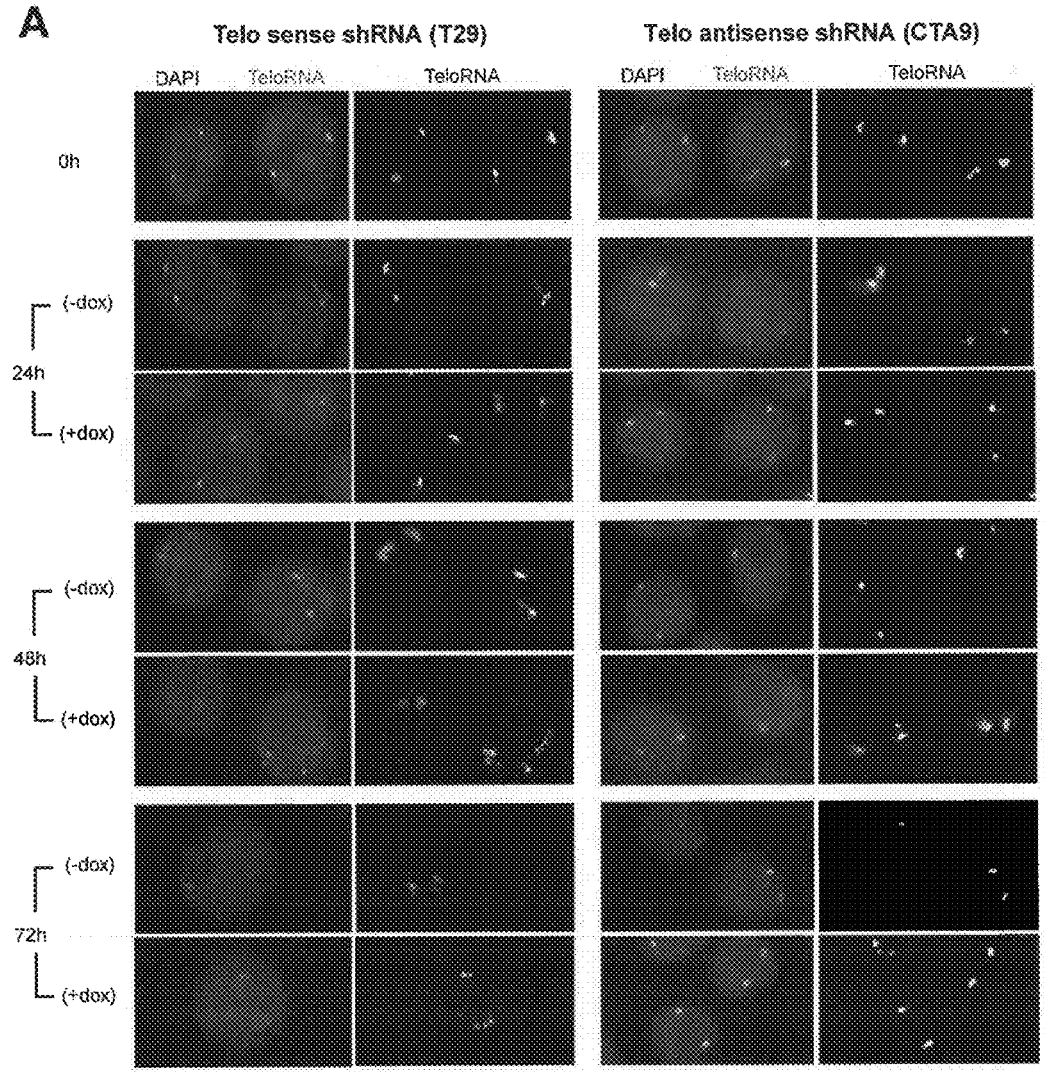
FIGS. 9A-9B show reduced growth rates in ES cells harboring shRNAs against telomeric RNA.
Figure 9:
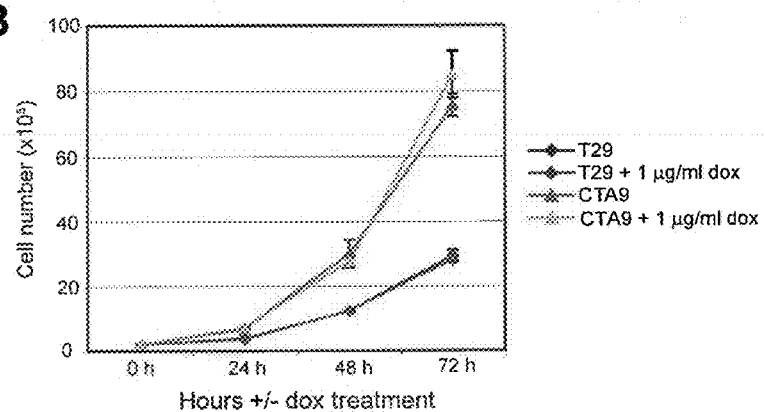

To test the functional significance of telomeric RNA expression, we generated male ES cells carrying shRNAs directed against the telomeric transcripts. Although we originally designed the shRNA constructs to be doxycycline-inducible, examination by RT-PCR showed leaky expression of the precursor shRNA. To determine if shRNA expression affected telomeric expression, we carried out RNA FISH using telomeric probes and found no obvious gross effects on accumulation of telomeric transcripts near the X and Y but did detect increased expression originating elsewhere in the genome, particularly during prolonged culture (FIG. 9A). Examination of growth rates indicated significant differences between male ES cell lines carrying shRNAs directed against sense (T29) versus antisense (CTA9) RNA strands. Indeed, the T29 clone, which harbored shRNAs against the expressed telomeric strand, grew at less than half the rate of the control CTA9 clone (FIG. 9B). This effect was reproducible in two independent biological replications of the experiment. Consistent with leakiness of the shRNA vector, the effect was observed regardless of whether cells were treated with doxycycline. Elevated telomeric signals of presumptive autosomal origin during prolonged culture (FIG. 9A) may indicate increased cellular stress due to the shRNA. Telomeric expression may therefore be involved in stem cell growth and maintenance of general cell health.

DISCUSSION

We have identified a new macroRNA associated with the sex chromosomes in the mouse. In ES cells, two foci of teloRNA accumulation are observed and appear as appendages to the sex chromosomes. Upon differentiation, the number of foci reduces to one and accumulation becomes specific to the heterochromatic sex chromosome—i.e., the Xi in female cells and the Y in male cells. In XX ES cells, teloRNA accumulation is substantial, resembling the Xist RNA 'cloud' that envelopes the Xi. While normal and apparently healthy cells make the transition from two to one sex-linked RNA cluster, epigenetically abnormal cells—such as those lacking dosage compensation and those derived from cancers—acquire deviant patterns of expression which includes no teloRNA foci, aberrantly large single foci, and multifocal expression.

On the basis of these observations, we propose that the pattern of teloRNA expression can be used as a cytological mark to distinguish clinically relevant physiological states. We suggest that pluripotent stem cells (e.g., ES cells) can be identified by the accumulation of two sex-linked teloRNA clusters and that differentiating and differentiated cell types can be identified by the reduction to one teloRNA cluster. We furthermore posit that any deviation from these patterns herald genotoxicity, malignancy, and other forms of epigenetic or physiological stress. Thus, the patterns of differential teloRNA expression could serve as a powerful tool to cull highly desirable stem cells from their differentiated counterparts and possibly also identify pre-malignant states.

Figure 2:
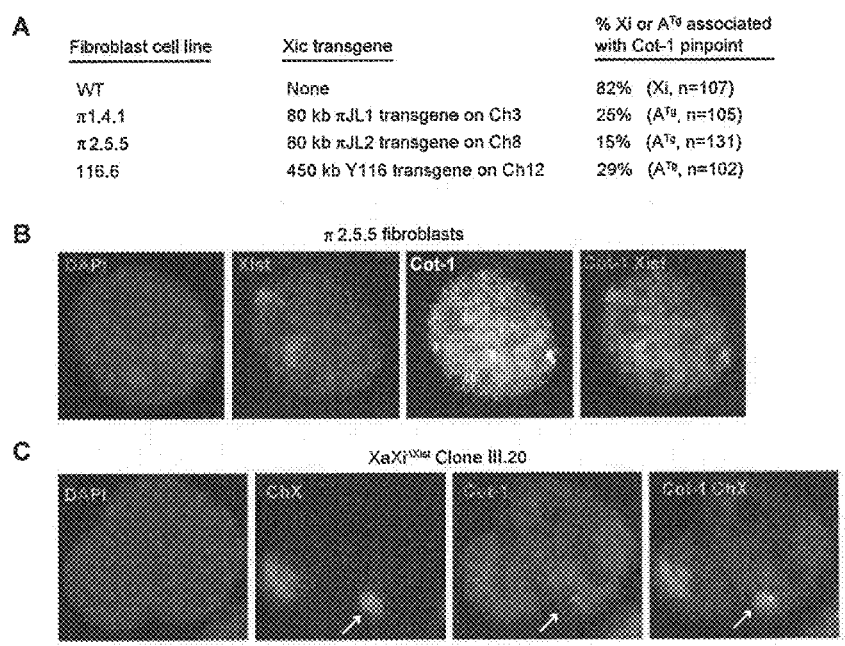
FIGS. 2A-2C show gain- and loss-of-function XCI mutations have no effect on Cot-1 pinpoint localization.

Why are telomeric repeats transcribed? It is curious that teloRNAs attach to both sex chromosomes in ES cells without involving autosomes and, once cells differentiate, teloRNAs mark only the heterochromatic sex chromosome (Xi, Y). One function of telomeric transcription may therefore be directly linked to chromosome expression states. For example, teloRNA expression may facilitate the recruitment of Xi and Y to a subnuclear compartment that establishes or maintains heterochromatin, especially in light of our recent finding that the Xi is maintained in a perinucleolar compartment (Zhang, et al., *Cell* 129:693-706 (2007)). At first glance, this scenario is not apparently supported by our analysis of Xist mutant cell lines, which showed no immediate impact of gaining or losing Xist expression on teloRNA (FIG. 2). However, it is known the $Xi^{\Delta xist}$ chromosome in the Xa $Xi^{\Delta xist}$ line does not reactivate immediately upon losing Xist expression (Zhang, et al., *Cell* 129: 693-706 (2007)); thus, $Xi^{\Delta xist}$'s association with teloRNA may persist for some time. It is also known that autosomes carrying Xist transgenes are often not as effectively silenced as the Xi (Lee, et al., *Proc Natl Acad Sci USA* 96:3836-3841 (1999); Lee and Jaenisch, *Nature* 386:275-279 (1997); Heard et al., *Proc Natl Acad Sci USA* 96:6841-6846 (1999)); perhaps the absence of teloRNA accumulation on the autosome precludes full silencing.

Clearly, autosomal telomeres can accumulate RNA as well, but they seem to do so only under stressful conditions, such as when dosage compensation fails or when cells undergo malignant transformation. It is tempting to speculate that teloRNA expression may also be linked to apoptosis, given that aberrant XCI and cell death lead to ectopic teloRNA accumulation (speckling) and that cancer cells—which often suppress apoptosis—frequently downregulate teloRNA expression. It is important to emphasize that, under normal conditions, autosomal telomeres may actually be transcribed, but without the accompanying RNA accumulation seen on the X and Y. The general teloRNA upregulation observed in Dcr−/− mutants makes post-transcriptional regulation a feasible mechanism of teloRNA control. In conclusion, our work adds to a growing list of macroRNAs that impact the epigenome and provides evidence that ncRNAs from multiple genetic pathways intersect to regulate gene expression.

Experimental Procedures
Cell Lines

The following ES cell lines have been described elsewhere: Wildtype female ES cell line, 16.7, and male ES line, J1 (Lee and Lu, *Cell* 99:47-57 (1999)); transgenic cell lines, π2.5.5, π1.4.1, and 116.6 (Lee and Jaenisch, *Nature* 386:

275-279 (1997)); and conditional knockout ES line, XaXi$^{Axist}$ (Zhang, et al., Cell 129:693-706 (2007)). MEFs were isolated from d13.5 embryos. Transformed fibroblast lines were immortalized by SV-40 T-antigen. The colon cancer line (HCC1937), ovarian cancer line (TOV12G), cervical cancer line (HeLa), and primary human fibroblast line (WI-35) have all been purchased from ATCC. HESC lines were maintained as described (Silva et al. Proc. Natl. Acad. Sci. USA 105:4820-4825 (2008)).

Dcr Targeting

Figure 8:
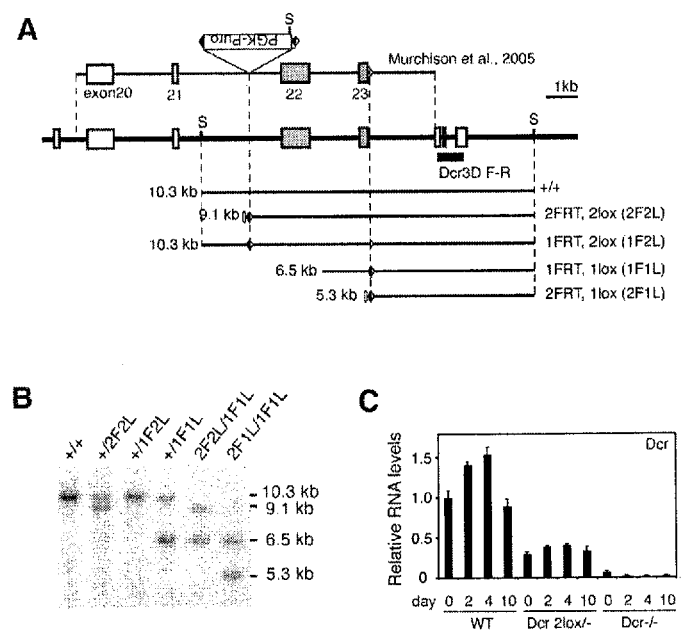
FIGS. 8A-8C show the generation of Dcr−/− ES cells.

The Dcr-deficient ES lines have been generated by Y. Ogawa (manuscript in preparation) using a targeting construct generously provided by Greg Hannon (Murchison et al., Proc Natl Acad Sci USA 102:12135-12140 (2005)). After targeting the first allele, pOG-Flep and pMC-CreN were sequentially transfected to delete sequences between FRT and LoxP sites, thus removing both Puro and Dcr exons 22 and 23. While Dcr 2lox/− lines were easily generated, Dcr−/− lines could not be derived in the 16.7 female background despite multiple attempts. This result is similar to the reported difficulty of deriving Dcr−/− male clones, which was overcome only by accumulation of secondary, undefined epigenetic or genetic changes to the Dcr+/− clones (Murchison, et al., Proc Natl Acad Sci USA 102: 12135-12140 (2005)). We circumvented this problem by introducing a low-expressor Dcr transgene into Dcr 2lox/− clones, as follows: We cloned mouse Dcr cDNA by assembly from four parts synthesized from total RNA of J1 male ES cell and ligating into pBluescriptII SK(−), yielding pBS-Dicer1. The cDNA parts were amplified using primers DcrRT-1, 5'-agctttgtaggtcttgaggtc-3' (SEQ ID NO: 1); DcrRT-2, 5'-agtgccggagtcattaacaac-3' (SEQ ID NO: 2); DcrRT-3, 5'-agtgccggagtcattaacaac-3' (SEQ ID NO: 3); DcrRT-4, 5'-agtgccggagtcattaacaac-3' (SEQ ID NO: 4), were amplified by the following primers, respectively, DcrN-F, 5'-ccagtgctgcagtaagctgtg-3' (SEQ ID NO: 5) and DcrN-R, 5'-aattagagatcggcgctcgtc-3' (SEQ ID NO: 6); DcrM-F, 5'-ctgaggatgacgatgatgacgaagaa-3' (SEQ ID NO: 7) and DcrM-R2, 5'-aagaggtagaacacagtaggc-3' (SEQ ID NO: 8); DcrM-F2, 5'-tattctccggcttgagaagcc-3' (SEQ ID NO: 9) and DcrM-R, 5'-gccgcagctggttaagtagcagcc-3' (SEQ ID NO: 10); DcrC-F, 5'-ggtaggtttctggaatccatc-3' (SEQ ID NO: 11) and DcrC-Rspe, 5'-ccactagtgccgtggagctgtggttctg-3' (SEQ ID NO: 12). To add an N-terminal Hemagglutinin (HA) tag or Kozak sequence, DcrN-F-HA, we co-amplified with 5'-ccggtacct-ggccaccatgggatacccctacgacgtgcccgactacgcaggcctgcagctcat-gacc-3' (SEQ ID NO: 13) (for HA) or DcrN-F-Kz, 5'-ccg-gtacctggccaccatggcaggcctgcagctcatg (SEQ ID NO: 14) (for Kozak) with DcrN-R2, tgagccagtgttcaagcacac (SEQ ID NO: 15), digested the amplicon with MscI and MfeI, and inserted them into the 5' region of an MscI/MfeI-digested pBS-Dicer1. The Dcr cDNA was then cloned into the tet-inducible expression vector, pTRE2hyg (Clontech), yielding pTRE2-HADcr1 (HA-tag) or pTRE2-KzDcr1 (+Kozak). pTet-Off repressor and pTRE2-KzDcr1 or pTRE2-HADcr1 were randomly integrated into ES cells by electroporation. Following Dcr1 transgene introduction, Dcr expression was shown to be <<5% of wildtype levels even when 'induced' (Ogawa et al., in preparation) (FIGS. 8A and 8B). This level of expression rescued cell viability and enabled targeting of the second endogenous Dcr1 allele. Probes for Southern analysis were PCR amplified by following primers 3D-F 5'-ggtctggcaggtgtactatcc-3' (SEQ ID NO: 16) and 3D-R 5'-agctgttaggaacctgaggct-3' (SEQ ID NO: 17) for SpeI blots and primers flox forward and flox reverse for XbaI blots.

DNA- and RNA-FISH

Cot-1 DNA (Invitrogen) was labeled with Cy3-12-dUTP (Amersham Biosciences) by Prime-It Fluor fluorescence labeling kit (Stratagene). 1 µl of Cot-1 DNA (1 µg/µl) was mixed with 10 µl random 9-mer primers and 27 µl water. Solution was heated at 95° C. for 5 min to denature DNA, incubated on ice 5 min for probe annealing. 9.2 µl 5×Nucleotide buffer, 0.8 µl Cy3-12-dUTP and 2 µl Klenow were then added into the reaction. The reaction was carried out at 37° C. for 30 min. Labeled DNA was ethanol precipitated and re-suspended in 50 µl hybridization buffer (probe concentration is labeled as 20 ng/µl). DNA Oligo probes for Telomeric RNA FISH were ordered from Integrated DNA Technologies: Telo1, (TAACCC)$_7$-Alexa488-3'; Telo2, (TTAGGG)$_6$-Alexa488-3'. Oligo probes were dissolved at 1 pmol/µl in hybridization buffer for RNA FISH. For combinational RNA FISH of Cot-1 and Telomeric RNA, Cot-1 probe and Telomeric DNA oligo probe were mixed at the final concentration of 20 ng/µl and 0.5 pmol/µl respectively. Slides were prepared by Shandon Cytospin3 cytocentrifuge (Shandon). Cells were fixed in 4% paraformaldehyde. Fluorescent images were collected on a Zeiss Axioplan2 microscope (Carl Zeiss Inc) using Openlab software (Improvision). Pictures of RNA and DNA FISH were collected in z-series (0.5µ z-interval, 3-4µ in total). Pictures from single focal plain are stacked and merged pictures carrying all the detectable signals within nuclei are shown. Additional details for RNA and DNA FISH have been described elsewhere (Zhang, et al., Cell 129:693-706 (2007)).

Northern Analyses

Probes used for Northern blots were as follows: Telo1-21 nt, TAACCCTAACCCTAACCCTAA (SEQ ID NO: 18); Telo2-21 nt, TTAGGGTTAGGGTTAGGGTTA (SEQ ID NO: 19); GAPDHprobe, GTAGACTCCACGACAT-ACTCAGCACCGGCCTCACCCCATT (SEQ ID NO: 20); miR-292-as: ACACTCAAAACCTGGCGGCACTT (SEQ ID NO: 21). Oligo probes were end-labeled using T4 polynucleotide kinase. Hybridization was carried out at 50° C. with ULTRAhyb™-Oligo Hybridization Buffer (Ambion). Northern blot protocol for small RNA detection has been described (Lau et al., Science 294:858-862 (2001)). Briefly, 20 µg of small RNAs extracted by mirVana miRNA Isolation Kit (Ambion) were used instead of total RNA and a 30mer oligo was used as probe to increase detection sensitivity (Telo1-30 nt: TAACCCTAACCCTAACCCTAAC-CCTAACCC (SEQ ID NO: 22)). All oligo probes were end-labeled using T4 polynucleotide kinase. Hybridization was carried out at either 50° C. (FIG. 7A) or 42° C. (FIG. 7C) with ULTRAhyb™-Oligo Hybridization Buffer (Ambion).

Generation and Analysis of shRNA Clones

The sense and antisense shRNA sequences were: Teloshpin-sense, 5'-TGCTGTTGACAGTGAGCGATTAGGGT-TAGGGTTAGGGTTATAGTGAAGCC ACAGATGTATA-ACCCTAACCCTAACCCTAACTGCCTACTGCCTC-GGA-3' (SEQ ID NO: 23); Teloshpin-antisense, 5'-TGCT-GTTGACAGTGAGCGATAACCCTAACCCTAAC-CCTAATAGTGAAGCC ACAGATGTATTAGGGT-TAGGGTTAGGGTTAGTGCCTACTGCCTCGGA-3' (SEQ ID NO: 24). Single-copy shRNA sequences were homologously targeted into male ES cells as follows. shRNAs were cloned into vector, p199, a lentiviral microRNA-based system for single-copy Pol-II-regulated RNAi in mammalian cells (Stegmeier et al., Proc. Natl. Acad. Sci. USA 102:13212-7 (2005)). The full shRNA-mir cassette was PCR-amplified by using the PCR primers: miR30for, 5'-GATGGCTGGGTACCTGTTTGAATGAGGCTTCA-3'

(SEQ ID NO: 25); miR30rev, 5'-GTCTAGAGGTCGA-CAAGTGATTTAATTTATACC-3' (SEQ ID NO: 26). The amplified product was then cloned into KpnI and SalI sites in pLox (Kyba et al., *Cell* 109:29-37 (2002)), a targeting vector that carries two features: (1) a Cre/LoxP-based system of site-specific integration into the male X-chromosome of Ainv15 ES cells, and (2) presumptive tet-inducibility of the shRNA insert. Twenty micrograms each of pLox derivatives and pSALK-CRE were electroporated into $4\times10^6$ Ainv15 cells in 800 µl of PBS at 4° C. (Bio-Rad Gene Pulser with the capacitance extender set to 500 µF and voltage set to 250 V). Electroporated cells were plated onto 10-cm dishes with neomycin-resistant MEFs, selected in 400 µg/ml G418 after 24 hours, and fed daily until colonies appeared from days 10-14. Integration was verified by PCR amplification using LoxinF (5-CTAGATCTCGAAGGATCTG-GAG-3 (SEQ ID NO: 27)) and LoxinR (5-ATACTTTCTCGGCAGGAGCA-3 (SEQ ID NO: 28)), which yield an insert-containing product of 500 bp.

For analysis of growth, T29 (sense) and CTA9 (antisense) shRNA clones were maintained in ES media containing 10% FBS with 1000 U/ml of LIF. On d0, the cells were plated in duplicate at a starting concentration of $\sim 2\times10^5$ cells/line onto T25 flasks containing irradiated male feeders. Cell growth was monitored for 72 h+/−doxycycline. Culture media was changed daily and 1 mg/ml of doxycycline was freshly added to +dox cultures every 24 h. Cell number was counted using a hemocytometer, and RNA FISH was performed as described above.

Example 2

RNA FISH

Below, we provide an exemplary protocol for RNA FISH that can be used in the methods of the invention for the detection of TeloRNA marks.

Preparation of Probe:

Probes are prepared using Boehringer Mannheim nick translation kit or Stratagene random prime labelling kit essentially as recommended by manufacturer. Generally, biotin-16-dUTP in combination with digoxigenin-11-dUTP is used. After labelling, the probe is precipitated with mouse Cot1 DNA (if your probe contains cross-hybridizing repetitive DNA) or yeast tRNA (if no repeats), 0.3M Na-acetate and 2 volumes EtOH at 4° C. for 1 hour. The probe is then spun and resuspended in hybridization buffer at 2 ng/µl probe DNA. Hybridization buffer: 50% formamide (American Bioanalytical), 2×SSC-pH7.4 (autoclaved), 2 mg/ml BSA (Boehringer Mannheim), 10% Dextran sulfate-500K (autoclaved). For hybridization, the probe is denatured at 75° C., 10 minutes. If probe contains repetitive elements, preanneal the probe at 42° C., 10-60 minutes using a Cot-1 cocktail (length of preannealling depends upon the repeats present). If the probe is a Cot-1 probe, skip the preannealing and use the probe immediately.

Preparation of Slides:

Cells are grown directly on 10-well slides (Fisher or Roboz). In general, fibroblasts stick better to glass slides if slides are precoated with 0.2% gelatin (Sigma) for 30 minutes at room temperature. Cells are then grown directly under a 100 µl drop of media, changing media daily.

When cells are 80-90% confluent, slides are fixed in cleaned Coplin jars as follows:
a) Immerse slides for 5 min.in ice-cold PBS.
b) Transfer to ice-cold CSK buffer (100 mM NaCl, 300 mM sucrose, 10 mM, PIPES-pH6.8, 3 mM $MgCl_2$) for 60 sec. PIPES needs to be pH'd before it can dissolve!
c) Immerse in CSK+0.5% Triton for 60 sec.
d) Re-equilibrate in CSK for 60 sec.
e) Fix in 4% paraformaldehyde in 1×PBS, pH 7.4 for 10 min. at room temperature. (Dissolve in 4 mM NaOH at 50° C., add 1/10 vol. 10×PBS after dissolved, and pH to 7.4 with Hcl). The fixative is good only for 3 weeks when stored in the dark at 4° C.
f) Store in 70% ethanol. RNA FISH should be performed within 1-2 weeks.

For hybridization, slides are dehydrated through 80%, 90%, 100% ethanol sequentially for 2 minutes each. Air dry slides at room temperature, <5 min. NOTE: Cells can also be cytospun onto glass slides (e.g., as would be required for seminiferous tubule spreads) or cytogenetically prepared by dropping methanol-acetic acid fixed cells onto glass slides.

Hybridization:

4-10 µl preannealed probe DNA is pipetted onto each well of slide (amount depends on the surface area of the prep) and covered with clean 18 mm×18 mm (for small surface areas) or 18×50 mm (for larger spots) cover slip (VWR). Optionally, the edges of cover slip can be sealed with rubber cement and incubate slide at 37° C. in a humid, dark chamber. The slide can be placed in a 150 $cm^2$ petri dish on two parallel slabs over Whatman paper moistened with water. The set-up is then placed inside a humidified tissue culture incubator and hybridized for a defined time. (Time is variable.)

Wash and Detection:

The slide is washed 3 times each for 5 minutes in 50% formamide, 2×SSC pH 7.4 at 45° C. and agitated lightly. The slide is then washed 3 times for 5 minutes each at 45° C. in 2×SSC pH 7.4 and agitated lightly. The slide is then blocked with 1% BSA (NEBL), 4×SSC, 0.1% Tween20 for 10 minutes at room temperature. For detection using a biotinylated probes, 1:400 dilution of avidin-conjugated fluorochrome (Vector) is used; for dig-labelled probes, 1:50 dilution of anti-digoxigenin antibody coupled to fluorochrome (Sigma, Fab fragments) is used. Dilutions are made in 1% BSA, 4×SSC, 0.1% Tween20. Incubate at 37° C. for 40 min. The slides are then washed 3 times for 10 minutes each at 45° C. in 4×SSC pH 7.4, 0.1% Tween20 and agitated lightly. Counterstain with DAPI for 5 minutes in 4×SSC and rinse once for 1 min. in 4×SSC.

3-10 µl Vectashield (Vector) mounting medium with anti-fade is applied to each well and coverslip is sealed with nail polish. The oil and dirt is wiped off with Windex and a kim wipe in preparation for oil immersion. The slides are ready for viewing under fluorescence microscopy.

Example 3

RNA/DNA FISH

Below, we provide an exemplary protocol for RNA/DNA FISH that can be used in the methods of the invention for the detection of TeloRNA marks.

Preparation of Probe:

The probes prepared using Boehringer Mannheim nick translation kit or Hi-Prime kit essentially as recommended by manufacturer. One preferred probe is biotin-16-dUTP in combination with digoxigenin-11-dUTP. After labelling, the probe is precipitated with mouse Cot1 DNA (if your probe contains cross-hybridizing repetitive DNA) or yeast tRNA, 0.3M Na-acetate and 2 volumes EtOH at 4° C. for 1 h, spun, and resuspended in hybridization buffer at 2 ng/µl probe DNA. Hybridization buffer: 50% formamide, 2×SSC, 2 mg/ml BSA, 10% Dextran sulfate-500K. For hybridization, the probe is denatured at 85° C., 10 minutes. If the probe contains repetitive elements, the probe is preannealed at 42° C., 10-60 minutes (length of preannealling depends upon the repeats present).

Preparation of Slides:

Cells are grown directly on 10-well slides (Roboz). In general, fibroblasts stick better to glass slides if slides are precoated with 0.2% gelatin (Sigma) for 30 minutes at room temperature. Cells are then grown directly under a 100 µl drop of media, changing media daily. When cells are 80-90% confluent, the cells are fixed as follows:
 a) Immerse slides for 5 min. on ice-cold PBS.
 b) Transfer to ice-cold CSK buffer (100 mM NaCl, 300 mM sucrose, 10 mM PIPES, 3 mM $MgCl_2$) for 30 sec.
 c) Immerse in CSK+0.5% Triton for 60 sec.
 d) Re-equilibrate in CSK for 60 sec.
 e) Fix in 4% paraformaldehyde (FLUKA) in PBS, pH 7.4 for 10 min. at room temperature.
 f) Store in 70% ethanol. RNA and DNAs stable for months under ethanol.

For hybridization, the slide is dehydrated through 80%, 90%, 100% ethanol sequentially for 2 min. each. The DNA is denatured by immersing slide in 70% formamide (American Bioanalytical), 2×SSC for 10 min. for 85° C. IMPORTANT: heat up the denaturation solution very slowly by putting coplin jar with solution in a water bath set initially at 50° C., then bring temperature up over 30-60 min. NOTE: The conditions for denaturation must be empirically determined. While DNA will reliably denature using these conditions, the RNA may move or degrade (probably depending on the gene of interest, cell type, and other uncontrollable factors).

Quench denaturation in ice-cold ethanol series as follows:
70% ethanol, 2 min.
80% ethanol, 2 min.
100% ethanol, 2 min.
100% ethanol, 2 min.

The slides are allowed to air dry at room temperature. Under phase contrast microscopy, examine cells to be sure they are still visible and intact. They should not look any different from before.

NOTE: Cells can also be cytospun onto glass slides or cytogenetically prepared by dropping methanol-acetic acid fixed cells onto glass slides.

Hybridization:

3 µl preannealed probe DNA is pipetted onto each well of 10-well slide or 10 ul for 8 mm cover slips and covered with clean 50 mm×50 mm cover slip (VWR; or Gold Seal, Clay Adams). The slides are incubated at 42° C. in a humid, dark chamber. In one example, the slide is placed in a pipet tip container with water at the bottom. The set-up is then placed inside a humidified tissue culture incubator. The hybridization takes place overnight.

Wash and Detection:

Slides are washed 2 times each for 5 minutes in 50% formamide, 2×SSC pH 7.4 at 45° C. and agitated lightly. Slides are washed 2 times for 5 minutes each at 45° C. in 2×SSC pH 7.4 and agitated lightly.

If the probe is not directly labelled with fluorophore, the slide is blocked with 1% BSA, 4×SSC for 10 minutes at room temperature. For biotinylated probes, a 1:400 dilution of avidin-conjugated fluorochrome is used; for dig-labelled probes, a 1:20 dilution of anti-digoxigenin antibody coupled to fluorochrome (Sigma, Fab fragments) is used. Dilutions are made in 1% BSA, 4×SSC. The detection system is incubated at room temperature for 30 minutes and washed 3 times for 5 minutes each at 45° C. in 4×SSC pH 7.4, 0.1% Tween20 and then agitated lightly.

For all probes, the slide is counterstained with DAPI (5 ul of 1 mg/ml stock into 50 ml of wash solution) for 2 minutes in 4×SSC and rinsed once for 2 minutes in 4×SSC. 3 µl of Vectashield (Vector) mounting medium with antifade is applied to each well and the coverslip is sealed with nail polish. The oil and dirt is wiped off with Windex and a kimwipe in preparation for oil immersion. Slides are then viewed under fluorescence microscopy.

Example 4

Exemplary Protocol for Sequential RNA/DNA FISH

In one example of the hybridization methods of the invention, a sequential RNA/DNA FISH technique is used. For this technique, Cot-1 DNA (Invitrogen) is labeled with Cy3-12-dUTP (Amersham Biosciences) by Prime-It Fluor fluorescence labeling kit (Stratagene). 1 µl of Cot-1 DNA (1 µg/µl) is mixed with 10 µl random 9-mer primers and 27 µl water. The solution is then heated at 95° C. for 5 minutes to denature DNA, incubated on ice 5 minutes for probe annealing. 9.2 µl 5×Nucleotide buffer, 0.8 µl Cy3-12-dUTP and 2 µl Klenow is then added into the reaction. The reaction is carried out at 37° C. for 30 minutes. Labeled DNA is subsequently ethanol precipitated and re-suspended in 50 µl hybridization buffer (probe concentration is labeled as 20 ng/µl). DNA Oligo probes for Telomeric RNA FISH can be ordered, for example, from Integrated DNA Technologies: e.g., $(TAACCC)_7$-Alexa488-3. Oligo probes are dissolved at 1 pmol/µl in hybridization buffer for RNA FISH. The standard RNA FISH protocol described above can then be used.

For combinational RNA FISH of Cot-1 and telomeric RNA, Cot-1 probe and Telomeric DNA oligo probe are mixed at the final concentration of 20 ng/µl and 0.5 pmol/µl respectively. Slides are prepared by cytospinning in Shandon Cytospin3 cytocentrifuge (Shandon). Cells are fixed in 4% paraformaldehyde after cytospinning onto glass slides. Fluorescent images are captured before the second round DNA FISH. For DNA FISH, cover slips of the RNA FISH slides are removed, the slides denatured in 70% formamide and 2×SSC for 10 minutes at 80° C. before chromosome painting probes are applied using the standard DNA FISH described above.

Pictures of RNA and DNA FISH are then overlaid and the location of the teloRNA relative to the X and Y can be determined.

In the above assay, ES cells are identified as pluripotent when a majority of the culture shows 2 telomeric teloRNA marks per diploid nucleus, one attached to each sex chromosome in the majority of cells. Cells are identified as differentiated or no longer pluriporent when 1 telomeric teloRNA mark is detected per diploid nucleus, attached to the heterochromatic sex chromosome (Xi in females, Y in males) in the majority of cells. Cells are identified as stressed, diseased, or aberrant cells when greater than 2 foci per diploid nucleus are detected. Usually many ectopic foci are detected, representing aberrant expression from multiple telomeres, not just the sex-linked ones.

Example 5

Exemplary Diagnostic Kit Components

Although the kits of the invention can include any of the components described herein, some exemplary components are provided below.

For use in RNA FISH methods of detection, the following components can be used.

The kit would have one or more components that would help the investigator identify the teloRNA mark, localize it to the sex chromosomes, and identify which is the inactive X (Xi).

Human XIST Riboprobe Cocktail

For detection of human XIST, a mixture of single-stranded RNA probes is directly labelled by fluorophores such as FITC or Cy3 (coupled to UTP). Various fragments from human XIST exons 1-8 are cloned into a T7 and SP6 expression vector and the riboprobes are synthesized by in vitro transcription using the T7 or SP6 polymerase. This enables specific detection of the 'sense' XIST strand, rather than the antisense TSIX strand. Alternatively, double-stranded plasmid or PCR probes covering the XIST gene body could be used to detect XIST, although no strand-specific information can be obtained using this approach. However, because only XIST forms an 'RNA cloud' around the Xi (TSIX does not), one can usually conclude that XCI has occurred based the occurrence of this RNA cloud.

Kit Components: human XIST riboprobe cocktail (10× concentration in hybridization buffer)—prelabelled with FITC; extra hybridization buffer for dilution; wash solutions; mounting media containing anti-fade and DAPI.

Telomeric RNA Probe

This is a single-stranded oligonucleotide probe labelled at the 3' end with a fluorophore. An example would be the 7mer of TAACCC: (TAACCC)$_7$-Alexa488-3'. This sequence is sufficient to identify the sex-linked pinpoint signal.

Human Cot-1 Probe

Alternatively, the user could employ the human heterogeneous Cot-1 probe: The Cot-1 fraction of the human genome is the first to reanneal after denaturation (reassociation kinetics). It contains the most highly repetitive elements in the mammalian genome, such as LINEs, SINEs, LTRs, and ERVs. Because Cot-1 sequences are often present in the intronic regions of genes, hybridization to a Cot-1 probe reveals regions of the genome which are undergoing new transcription (unspliced nascent RNA). Cot-1 DNA can be purchased from Promega. We then label it with fluorophores and hybridize to fixed nuclei.

Kit Components Pre-labelled Cot-1 DNA, either with FITC or Cy3 or Cy5.

Additional components that can be included in the kits of the invention include a chromosome painting kit to check karyotype. This type of kit is commercially available, for example, from Cambio UK. Components for the detection of human X-chromosome or human Y-chromosome can also be included.

Other Embodiments

All publications, patent applications, and patents, mentioned in this specification, including PCT Application Nos. PCT/US06/025800, filed on Jun. 30, 2006; PCT/US08/000, 959, filed on Jan. 24, 2008; PCTUS08/003,260, filed on Mar. 12, 2008; and U.S. Provisional Application No. 61/010,615, filed on Jan. 10, 2008, are incorporated herein by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A method for determining the differentiation state of a pluripotent stem cell, wherein said stem cell is one of a population of stem cells, said method comprising:
   (a) contacting said stem cell with a heterogeneous Cot-1 nucleic acid probe under conditions for hybridization of the heterogeneous Cot-1 nucleic acid probe to a ribonucleic acid molecule in the nucleus of said stem cell; and
   (b) detecting the hybridization of said heterogeneous Cot-1 nucleic acid probe to the ribonucleic acid molecule in the stem cell, wherein the hybridization of the heterogeneous Cot-1 nucleic acid probe to the ribonucleic acid molecule in the stem cell is detected as a teloRNA mark in situ using fluorescent in situ hybridization (FISH),
   wherein the presence of two teloRNA marks, one on each sex chromosome, identifies said stem cell as a stem cell that is undifferentiated and the presence of only one teloRNA mark on an inactive X chromosome in a female stem cell or a Y chromosome in a male stem cell identifies said stem cell as a stem cell that is differentiated.

2. The method of claim 1, wherein said Cot-1 nucleic acid probe hybridizes to a telomeric repeat sequence or a subtelomeric sequence.

3. The method of claim 2, wherein said Cot-1 probe comprises at least one copy of the telomeric repeat sequence TAACCC, or a frameshift thereof.

4. The method of claim 1, wherein said cell is an embryonic stem cell.

5. A method for determining the differentiation state of a pluripotent stem cell, wherein said stem cell is one of a population of stem cells, said method comprising:
   (a) contacting said stem cell with a telomeric nucleic acid probe comprising at least one copy of a TAACCC nucleic acid sequence under conditions for hybridization of the telomeric nucleic acid probe to a ribonucleic acid molecule in the nucleus of said stem cell; and
   (b) detecting the hybridization of said telomeric nucleic acid probe to the ribonucleic acid molecule in the stem cell in situ using fluorescent in situ hybridization (FISH), wherein the hybridization of the telomeric nucleic acid probe to the ribonucleic acid molecule in the stem cell is detected as a teloRNA mark, wherein the presence of two teloRNA marks, one on each sex chromosome, identifies said stem cell as a stem cell that is undifferentiated and the presence of only one teloRNA mark on an inactive X chromosome in a female stem cell or a Y chromosome in a male stem cell identifies said stem cell as a stem cell that is differentiated.

6. The method of claim 5, wherein the hybridization is at high stringency.

7. The method of claim 5, wherein the nucleus is undenatured.

8. The method of claim 5, wherein said telomeric nucleic acid probe hybridizes to a telomeric repeat sequence.

9. The method of claim 5, wherein said telomeric nucleic acid probe comprises a frameshift of said TAACCC nucleic acid sequence.

10. The method of claim 5, wherein said telomeric nucleic acid probe comprises three to seven copies of the nucleic acid sequence TAACCC or a frameshift thereof.

11. The method of claim 5, wherein said cell is an embryonic stem cell.

12. The method of claim 5, further comprising determining the presence or absence of at least one X-chromosome inactivation (XCI) marker in said stem cell, wherein the presence of said XCI marker identifies said stem cell in said population of stem cells as a stem cell that is differentiated and the absence of said XCI marker identifies said stem cell as a cell that is undifferentiated.

13. The method of claim 5, further comprising detecting at least one polypeptide pluripotency marker selected from the group consisted of Oct4, Nanog, Rex1, stage specific embryonic antigen (SSEA)-1, SSEA-3, and SSEA-4, wherein the presence of a polypeptide pluripotency marker identifies said stem cell as a stem cell that is undifferentiated.

14. A method for determining the differentiation state of a pluripotent stem cell culture, said method comprising:

(a) contacting said stem cell culture with a telomeric nucleic acid probe comprising at least one copy of a TAACCC nucleic acid sequence or a heterogeneous Cot-1 nucleic acid probe under conditions for hybridization of the telomeric nucleic acid probe or Cot-1 nucleic acid probe to ribonucleic acid molecules in the nuclei of stem cells in said stem cell culture; and (b) detecting the hybridization of said telomeric nucleic acid probe or Cot-1 nucleic acid probe to the ribonucleic acid molecules in the stem cells in situ using fluorescent in situ hybridization (FISH) in said stem cell culture, wherein the hybridization of the telomeric nucleic acid probe or Cot-1 nucleic acid probe to the ribonucleic acid molecules in the stem cells appears as a teloRNA mark, wherein the presence of two teloRNA marks, one on each sex chromosome, in at least 5% of the cells in said stem cell culture identifies said stem cell culture as undifferentiated.

15. The method of claim 1, wherein said cell is an induced pluripotent stem cell (iPS).

16. The method of claim 5, wherein said cell is an induced pluripotent stem cell (iPS).

* * * * *